(12) United States Patent
Horowitz

(10) Patent No.: US 11,633,202 B1
(45) Date of Patent: *Apr. 25, 2023

(54) CATHETER BASED RETRIEVAL DEVICE WITH PROXIMAL BODY HAVING AXIAL FREEDOM OF MOVEMENT

(71) Applicant: Retriever Medical, Inc., Las Vegas, NV (US)

(72) Inventor: Michael Bruce Horowitz, Naples, FL (US)

(73) Assignee: Retriever Medical, Inc., Irvine, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/694,036

(22) Filed: Mar. 14, 2022

Related U.S. Application Data

(60) Continuation of application No. 17/127,521, filed on Dec. 18, 2020, which is a continuation of application
(Continued)

(51) Int. Cl.
*A61B 17/22* (2006.01)
*A61B 17/221* (2006.01)
(Continued)

(52) U.S. Cl.
CPC ...... *A61B 17/22032* (2013.01); *A61B 17/221* (2013.01); *A61B 2017/00867* (2013.01);
(Continued)

(58) Field of Classification Search
CPC ............ A61B 17/22032; A61B 17/221; A61B 2017/00867; A61B 2017/22038;
(Continued)

(56) References Cited

U.S. PATENT DOCUMENTS

| 2,955,592 A | 10/1960 | MacLean |
| 3,435,826 A | 4/1969 | Fogarty |

(Continued)

FOREIGN PATENT DOCUMENTS

| AU | 2015210338 | 8/2015 |
| CN | 102186427 | 9/2011 |

(Continued)

OTHER PUBLICATIONS

PCT/US18/55606, "International Application Serial No. PCT/US18/55606, International Search Report and Written Opinion dated Feb. 14, 2019", Horowitz, Michael Bruce, 12 pages.
(Continued)

*Primary Examiner* — Richard G Louis
(74) *Attorney, Agent, or Firm* — Francis Law Group

(57) ABSTRACT

Provided herein are methods and systems for the removal of anatomical occlusions, and an occlusion removal device comprising a first body adapted to be mounted to a delivery wire and releasably engaged to the delivery wire, wherein while engaged the first body remains fixed on the delivery wire and upon release moves axially along the delivery wire, and a second body adapted to be mounted to the delivery wire. A first proximal body may be oriented proximally to a second distal body. The proximal body and the distal body may be adapted to expand upon exiting a delivery catheter. The proximal body may be releasably engaged by a mechanically breakable connection or an electrolytically or heat disconnectable connection, the electrolytically disconnectable connection being broken upon an application of electric current to the electrolytically disconnectable connection.

5 Claims, 20 Drawing Sheets

Related U.S. Application Data

No. 16/205,632, filed on Nov. 30, 2018, now Pat. No. 10,898,215, which is a division of application No. 15/953,151, filed on Apr. 13, 2018, now Pat. No. 10,172,634.

(60) Provisional application No. 62/653,247, filed on Apr. 5, 2018, provisional application No. 62/589,613, filed on Nov. 22, 2017, provisional application No. 62/606,993, filed on Oct. 16, 2017, provisional application No. 62/573,006, filed on Oct. 16, 2017.

(51) Int. Cl.
  *A61B 17/00* (2006.01)
  *A61M 25/10* (2013.01)

(52) U.S. Cl.
  CPC ............... *A61B 2017/22038* (2013.01); *A61B 2017/22051* (2013.01); *A61B 2017/22054* (2013.01); *A61B 2017/22072* (2013.01); *A61B 2017/22079* (2013.01); *A61B 2017/22094* (2013.01); *A61M 2025/1013* (2013.01); *A61M 2025/1015* (2013.01)

(58) Field of Classification Search
  CPC ........... A61B 2017/22051; A61B 2017/22054; A61B 2017/22072; A61B 2017/22079; A61B 2017/22094; A61M 2025/1013; A61M 2025/1015
  See application file for complete search history.

(56) References Cited

U.S. PATENT DOCUMENTS

| | | | |
|---|---|---|---|
| 3,923,065 | A | 12/1975 | Nozick |
| 4,030,503 | A | 6/1977 | Clark, III |
| 4,243,040 | A | 1/1981 | Beecher |
| 4,643,184 | A | 2/1987 | Mobin-Uddin |
| 4,646,736 | A | 3/1987 | Auth |
| 4,650,466 | A | 3/1987 | Luther |
| 5,059,178 | A | 10/1991 | Ya |
| 5,192,286 | A | 3/1993 | Phan |
| 5,192,290 | A | 3/1993 | Hilal |
| 5,383,887 | A | 1/1995 | Nadal |
| 5,419,774 | A | 5/1995 | Willard |
| 5,476,450 | A | 12/1995 | Ruggio |
| 5,490,859 | A | 2/1996 | Mische |
| 5,683,451 | A | 11/1997 | Lenker |
| 5,769,816 | A | 6/1998 | Barbut |
| 5,800,457 | A | 9/1998 | Gelbfish |
| 5,817,104 | A | 10/1998 | Bilitz |
| 5,827,229 | A | 10/1998 | Auth |
| 5,846,251 | A | 12/1998 | Hart |
| 5,855,578 | A | 1/1999 | Guglielmi |
| 5,869,079 | A | 2/1999 | Wong |
| 5,954,737 | A | 9/1999 | Lee |
| 5,971,938 | A | 10/1999 | Hart |
| 6,022,888 | A | 2/2000 | Morishige |
| 6,068,645 | A | 5/2000 | Tu |
| 6,126,635 | A | 10/2000 | Simpson |
| 6,146,396 | A | 11/2000 | Konya |
| 6,152,946 | A | 11/2000 | Broome |
| 6,168,579 | B1 | 1/2001 | Tsugita |
| 6,179,859 | B1 | 1/2001 | Bates |
| 6,183,481 | B1 | 2/2001 | Lee |
| 6,221,006 | B1 | 4/2001 | Dubrul |
| 6,238,412 | B1 | 5/2001 | Dubrul |
| 6,245,076 | B1 | 6/2001 | Yan |
| 6,245,089 | B1 | 6/2001 | Daniel |
| 6,258,115 | B1 | 7/2001 | Dubrul |
| 6,264,663 | B1 | 7/2001 | Cano |
| 6,264,671 | B1 | 7/2001 | Stack |
| 6,322,572 | B1 | 11/2001 | Lee |
| 6,364,895 | B1 | 4/2002 | Greenhalgh |
| 6,371,953 | B1 | 4/2002 | Beyar |
| 6,383,205 | B1 | 5/2002 | Samson |
| 6,413,235 | B1 | 7/2002 | Parodi |
| 6,423,032 | B2 | 7/2002 | Parodi |
| 6,432,122 | B1 | 8/2002 | Gilson |
| 6,447,530 | B1 | 9/2002 | Ostrovsky |
| 6,485,502 | B2 | 11/2002 | Don Michael |
| 6,508,782 | B1 | 1/2003 | Evans |
| 6,511,492 | B1 | 1/2003 | Rosenbluth |
| 6,514,273 | B1 | 2/2003 | Voss |
| 6,530,923 | B1 | 3/2003 | Dubrul |
| 6,530,934 | B1 | 3/2003 | Jacobsen |
| 6,530,935 | B2 | 3/2003 | Wensel |
| 6,544,276 | B1 | 4/2003 | Azizi |
| 6,544,279 | B1 | 4/2003 | Hopkins |
| 6,551,342 | B1 | 4/2003 | Shen |
| 6,575,995 | B1 | 6/2003 | Huter |
| 6,589,263 | B1 | 7/2003 | Hopkins |
| 6,596,011 | B2 | 7/2003 | Johnson |
| 6,602,271 | B2 | 8/2003 | Adams |
| 6,605,074 | B2 | 8/2003 | Zadno-Azizi |
| 6,605,102 | B1 | 8/2003 | Mazzocchi |
| 6,610,077 | B1 | 8/2003 | Hancock |
| 6,660,014 | B2 | 12/2003 | Demarais |
| 6,699,260 | B2 | 3/2004 | Dubrul |
| 6,755,847 | B2 | 6/2004 | Eskuri |
| 6,767,353 | B1 | 7/2004 | Shiber |
| 6,790,204 | B2 | 9/2004 | Zadno-Azizi |
| 6,800,080 | B1 | 10/2004 | Bates |
| 6,808,520 | B1 | 10/2004 | Fourkas |
| 6,824,545 | B2 | 11/2004 | Sepetka |
| 6,833,002 | B2 | 12/2004 | Stack |
| 6,902,540 | B2 | 6/2005 | Dorros |
| 6,939,361 | B1 | 9/2005 | Kleshinski |
| 6,945,977 | B2 | 9/2005 | Demarais |
| 7,004,954 | B1 | 2/2006 | Voss |
| 7,013,845 | B1 | 3/2006 | McFarland |
| 7,025,751 | B2 | 4/2006 | Silva |
| 7,052,500 | B2 | 5/2006 | Bashiri |
| 7,056,328 | B2 | 6/2006 | Arnott |
| 7,063,707 | B2 | 6/2006 | Bose |
| 7,094,249 | B1 | 8/2006 | Broome |
| 7,179,273 | B1 | 2/2007 | Palmer |
| 7,232,432 | B2 | 6/2007 | Fulton, III |
| 7,285,126 | B2 | 10/2007 | Sepetka |
| 7,306,618 | B2 | 12/2007 | Demond |
| 7,320,698 | B2 | 1/2008 | Eskuri |
| 7,323,002 | B2 | 1/2008 | Johnson |
| 7,578,830 | B2 | 8/2009 | Kusleika |
| 7,645,290 | B2 | 1/2010 | Lucas |
| 7,686,825 | B2 | 3/2010 | Hauser |
| 7,691,121 | B2 | 4/2010 | Rosenbluth |
| 7,763,010 | B2 | 7/2010 | Evans |
| 7,766,934 | B2 | 8/2010 | Pal |
| 7,780,696 | B2 | 8/2010 | Daniel |
| 7,798,992 | B2 | 9/2010 | Ortiz |
| 7,799,049 | B2 | 9/2010 | Ostrovsky |
| 7,931,659 | B2 | 4/2011 | Bose |
| 7,938,820 | B2 | 5/2011 | Webster |
| 7,993,302 | B2 | 8/2011 | Hebert |
| 7,993,363 | B2 | 8/2011 | Demond |
| 8,057,496 | B2 | 11/2011 | Fischer, Jr. |
| 8,070,769 | B2 | 12/2011 | Broome |
| 8,070,791 | B2 | 12/2011 | Ferrera |
| 8,075,510 | B2 | 12/2011 | Aklog |
| 8,100,935 | B2 | 1/2012 | Rosenbluth |
| 8,252,020 | B2 | 8/2012 | Hauser |
| 8,273,116 | B2 | 9/2012 | Licata |
| RE43,902 | E | 1/2013 | Hopkins |
| 8,366,735 | B2 | 2/2013 | Bose |
| 8,403,976 | B2 | 3/2013 | Sachar |
| 8,460,312 | B2 | 6/2013 | Bose |
| 8,486,105 | B2 | 7/2013 | Demond |
| 8,585,713 | B2 | 11/2013 | Ferrera |
| 8,734,374 | B2 | 5/2014 | Aklog |
| 8,758,424 | B2 | 6/2014 | Sachar |
| 8,771,289 | B2 | 7/2014 | Mohiuddin |
| 8,784,434 | B2 | 7/2014 | Rosenbluth |
| 8,784,441 | B2 | 7/2014 | Rosenbluth |

(56) References Cited

U.S. PATENT DOCUMENTS

| | | |
|---|---|---|
| 8,784,442 B2 | 7/2014 | Jones |
| 8,795,305 B2 | 8/2014 | Martin |
| 8,801,748 B2 | 8/2014 | Martin |
| 8,821,476 B2 | 9/2014 | Agah |
| 8,892,182 B2 | 11/2014 | Matonick |
| 8,900,179 B2 | 12/2014 | Jenson |
| 8,945,143 B2 | 2/2015 | Ferrera |
| 8,956,386 B2 | 2/2015 | Hauser |
| 8,968,330 B2 | 3/2015 | Rosenbluth |
| 8,974,512 B2 | 3/2015 | Aboytes |
| 8,998,947 B2 | 4/2015 | Aboytes |
| 9,078,658 B2 | 7/2015 | Hewitt |
| 9,119,656 B2 | 9/2015 | Bose |
| 9,149,609 B2 | 10/2015 | Ansel |
| 9,155,552 B2 | 10/2015 | Ulm, III |
| 9,198,670 B2 | 12/2015 | Hewitt |
| 9,204,887 B2 | 12/2015 | Cully |
| 9,211,396 B2 | 12/2015 | Aboytes |
| 9,259,237 B2 | 2/2016 | Quick |
| 9,295,473 B2 | 3/2016 | Hewitt |
| 9,351,747 B2 | 5/2016 | Kugler |
| 9,358,022 B2 | 6/2016 | Morsi |
| 9,402,938 B2 | 8/2016 | Aklog |
| 9,408,620 B2 | 8/2016 | Rosenbluth |
| 9,408,626 B2 | 8/2016 | Tekulve |
| 9,427,252 B2 | 8/2016 | Sos |
| 9,439,664 B2 | 9/2016 | Sos |
| 9,445,828 B2 | 9/2016 | Turjman |
| 9,456,834 B2 | 10/2016 | Folk |
| 9,463,035 B1 | 10/2016 | Greenhalgh |
| 9,463,036 B2 | 10/2016 | Brady |
| 9,492,174 B2 | 11/2016 | Hewitt |
| 9,510,854 B2 | 12/2016 | Mallaby |
| 9,510,930 B2 | 12/2016 | Patel |
| 9,526,864 B2 | 12/2016 | Quick |
| 9,526,865 B2 | 12/2016 | Quick |
| 9,579,116 B1 | 2/2017 | Nguyen |
| 9,597,087 B2 | 3/2017 | Marchand |
| 9,615,832 B2 | 4/2017 | Bose |
| 9,636,206 B2 | 5/2017 | Nguyen |
| 9,655,633 B2 | 5/2017 | Leynov |
| 9,655,999 B2 | 5/2017 | Bettinger |
| 9,662,137 B2 | 5/2017 | Jenson |
| 9,700,332 B2 | 7/2017 | Marchand |
| 9,707,071 B2 | 7/2017 | Sachar |
| 9,717,514 B2 | 8/2017 | Martin |
| 9,717,519 B2 | 8/2017 | Rosenbluth |
| 9,744,024 B2 | 8/2017 | Nguyen |
| 9,827,084 B2 | 11/2017 | Bonnette |
| 9,844,382 B2 | 12/2017 | Aboytes |
| 9,844,386 B2 | 12/2017 | Nguyen |
| 9,844,387 B2 | 12/2017 | Marchand |
| 9,848,975 B2 | 12/2017 | Hauser |
| 9,855,051 B2 | 1/2018 | Aboytes |
| 9,855,052 B2 | 1/2018 | Aboytes |
| 9,883,877 B2 | 2/2018 | Look |
| 9,943,321 B2 | 4/2018 | Nita |
| 9,943,397 B2 | 4/2018 | Bonnette |
| 9,962,178 B2 | 5/2018 | Greenhalgh |
| 9,968,472 B2 | 5/2018 | Sachar |
| 9,999,493 B2 | 6/2018 | Nguyen |
| 10,004,531 B2 | 6/2018 | Rosenbluth |
| 10,010,335 B2 | 7/2018 | Greenhalgh |
| 10,016,266 B2 | 7/2018 | Hauser |
| 10,028,759 B2 | 7/2018 | Wallace |
| 10,034,966 B2 | 7/2018 | Bettinger |
| 10,045,790 B2 | 8/2018 | Cox |
| 10,070,879 B2 | 9/2018 | Nguyen |
| 10,098,651 B2 | 10/2018 | Marchand |
| 10,123,814 B2 | 11/2018 | Bashir |
| 10,143,482 B2 | 12/2018 | Nguyen |
| 10,172,634 B1 | 1/2019 | Horowitz |
| 10,194,897 B2 | 2/2019 | Cedro, Jr. |
| 10,238,406 B2 | 3/2019 | Cox |
| 10,238,482 B2 | 3/2019 | Nguyen |
| 10,258,357 B1 | 4/2019 | Horowitz |
| 10,271,864 B2 | 4/2019 | Greenhalgh |
| 10,292,805 B2 | 5/2019 | Sachar |
| 10,327,883 B2 | 6/2019 | Yachia |
| 10,335,186 B2 | 7/2019 | Rosenbluth |
| 10,342,571 B2 | 7/2019 | Marchand |
| 10,349,960 B2 | 7/2019 | Quick |
| 10,376,275 B2 | 8/2019 | Nguyen |
| 10,383,644 B2 | 8/2019 | Molaei |
| 10,383,983 B2 | 8/2019 | Aklog |
| 10,456,236 B2 | 10/2019 | Nguyen |
| 10,492,805 B2 | 12/2019 | Culbert |
| 10,512,478 B2 | 12/2019 | Greenhalgh |
| 10,512,479 B2 | 12/2019 | Nguyen |
| 10,517,617 B2 | 12/2019 | Aklog |
| 10,517,624 B2 | 12/2019 | Wallace |
| 10,524,811 B2 | 1/2020 | Marchand |
| 10,561,431 B2 | 2/2020 | Greenhalgh |
| 10,588,655 B2 | 3/2020 | Rosenbluth |
| 10,588,656 B2 | 3/2020 | Trosper |
| 10,610,245 B2 | 4/2020 | Wallace |
| 10,695,159 B2 | 6/2020 | Hauser |
| 10,702,367 B2 | 7/2020 | Sachar |
| 10,709,471 B2 | 7/2020 | Rosenbluth |
| 10,716,583 B2 | 7/2020 | Look |
| 10,743,907 B2 | 8/2020 | Bruzzi |
| 10,779,843 B2 | 9/2020 | Wallace |
| 10,779,852 B2 | 9/2020 | Bruzzi |
| 10,799,331 B2 | 10/2020 | Hauser |
| 10,806,559 B2 | 10/2020 | Bonnette |
| 10,813,663 B2 | 10/2020 | Bruzzi |
| 10,835,268 B2 | 11/2020 | Wallace |
| 10,835,269 B1 | 11/2020 | Wallace |
| 10,842,513 B2 | 11/2020 | Greenhalgh |
| 10,849,730 B2 | 12/2020 | Sachar |
| 10,856,894 B2 | 12/2020 | Wallace |
| 10,863,999 B2 | 12/2020 | Wallace |
| 10,874,421 B2 | 12/2020 | Bruzzi |
| 10,888,342 B2 | 1/2021 | Wallace |
| 10,888,343 B2 | 1/2021 | Wallace |
| 10,898,215 B2 | 1/2021 | Horowitz |
| 10,912,576 B2 | 2/2021 | Wallace |
| 10,912,577 B2 | 2/2021 | Marchand |
| 10,932,929 B2 | 3/2021 | Sachar |
| 10,959,750 B2 | 3/2021 | Wallace |
| 10,993,731 B2 | 5/2021 | Leynov |
| 11,000,682 B2 | 5/2021 | Merritt |
| 11,026,709 B2 | 6/2021 | Greenhalgh |
| 11,058,445 B2 | 7/2021 | Cox |
| 11,058,451 B2 | 7/2021 | Marchand |
| 11,103,265 B2 | 8/2021 | Wallace |
| 11,147,571 B2 | 10/2021 | Cox |
| 11,154,314 B2 | 10/2021 | Quick |
| 11,166,802 B2 | 11/2021 | Sachar |
| 2001/0041909 A1 | 11/2001 | Tsugita |
| 2002/0022858 A1 | 2/2002 | Demond |
| 2002/0026211 A1 | 2/2002 | Khosravi |
| 2002/0032455 A1 | 3/2002 | Boock |
| 2002/0049452 A1 | 4/2002 | Kurz |
| 2002/0062119 A1* | 5/2002 | Zadno-Azizi ............ A61F 2/01 604/509 |
| 2002/0072764 A1 | 6/2002 | Sepetka |
| 2002/0111648 A1 | 8/2002 | Kusleika |
| 2002/0120277 A1 | 8/2002 | Hauschild |
| 2002/0133217 A1 | 9/2002 | Sirhan |
| 2002/0138097 A1 | 9/2002 | Ostrovsky |
| 2002/0156457 A1 | 10/2002 | Fisher |
| 2002/0161392 A1 | 10/2002 | Dubrul |
| 2002/0169474 A1 | 11/2002 | Kusleika |
| 2002/0173819 A1 | 11/2002 | Leeflang |
| 2002/0173835 A1 | 11/2002 | Bourang |
| 2002/0188276 A1 | 12/2002 | Evans |
| 2003/0004568 A1 | 1/2003 | Ken |
| 2003/0073953 A1 | 4/2003 | Mische |
| 2003/0083693 A1 | 5/2003 | Daniel |
| 2003/0100919 A1 | 5/2003 | Hopkins |
| 2003/0208224 A1 | 11/2003 | Broome |
| 2004/0039412 A1 | 2/2004 | Isshiki |
| 2004/0068288 A1 | 4/2004 | Palmer |

(56) References Cited

U.S. PATENT DOCUMENTS

| | | | |
|---|---|---|---|
| 2004/0073243 A1 | 4/2004 | Sepetka | |
| 2004/0098033 A1 | 5/2004 | Leeflang | |
| 2004/0133232 A1 | 7/2004 | Rosenbluth | |
| 2004/0138692 A1 | 7/2004 | Phung | |
| 2004/0167567 A1 | 8/2004 | Cano | |
| 2004/0199201 A1 | 10/2004 | Kellett | |
| 2004/0199202 A1 | 10/2004 | Dubrul | |
| 2004/0260333 A1* | 12/2004 | Dubrul | A61M 29/02 606/200 |
| 2005/0085846 A1 | 4/2005 | Carrison | |
| 2005/0187570 A1 | 8/2005 | Nguyen | |
| 2005/0197667 A1 | 9/2005 | Chan | |
| 2005/0209633 A1 | 9/2005 | Callister | |
| 2006/0095116 A1 | 5/2006 | Bolduc | |
| 2006/0100662 A1 | 5/2006 | Daniel | |
| 2006/0155305 A1 | 7/2006 | Freudenthal | |
| 2006/0253145 A1 | 11/2006 | Lucas | |
| 2007/0014831 A1 | 1/2007 | Sung | |
| 2007/0049903 A1 | 3/2007 | Jansen | |
| 2007/0100414 A1 | 5/2007 | Licata | |
| 2007/0106302 A1 | 5/2007 | Ortiz | |
| 2007/0128246 A1 | 6/2007 | Hossainy | |
| 2007/0156170 A1 | 7/2007 | Hancock | |
| 2007/0185500 A1 | 8/2007 | Martin | |
| 2007/0208367 A1* | 9/2007 | Fiorella | A61B 17/22 606/198 |
| 2007/0299466 A1 | 12/2007 | Sachar | |
| 2009/0054918 A1 | 2/2009 | Henson | |
| 2009/0062726 A1 | 3/2009 | Ford | |
| 2009/0105722 A1 | 4/2009 | Fulkerson | |
| 2009/0292307 A1 | 11/2009 | Razack | |
| 2009/0299393 A1 | 12/2009 | Martin | |
| 2009/0311300 A1 | 12/2009 | Wittchow | |
| 2010/0016867 A1 | 1/2010 | Itoh | |
| 2010/0042136 A1 | 2/2010 | Berrada | |
| 2010/0063572 A1 | 3/2010 | Teoh | |
| 2010/0087850 A1 | 4/2010 | Razack | |
| 2010/0114113 A1 | 5/2010 | Dubrul | |
| 2010/0204712 A1 | 8/2010 | Mallaby | |
| 2010/0268251 A1 | 10/2010 | Chen | |
| 2010/0268264 A1 | 10/2010 | Bonnette | |
| 2011/0125181 A1 | 5/2011 | Brady | |
| 2011/0130827 A1 | 6/2011 | Brodbeck | |
| 2011/0152823 A1 | 6/2011 | Mohiuddin | |
| 2011/0196414 A1 | 8/2011 | Porter | |
| 2011/0202088 A1* | 8/2011 | Eckhouse | A61B 17/221 606/200 |
| 2011/0213290 A1 | 9/2011 | Chin | |
| 2011/0213403 A1 | 9/2011 | Aboytes | |
| 2011/0251629 A1 | 10/2011 | Galdonik | |
| 2011/0288572 A1 | 11/2011 | Martin | |
| 2012/0123466 A1 | 5/2012 | Porter | |
| 2012/0172917 A1 | 7/2012 | Fifer | |
| 2012/0179181 A1 | 7/2012 | Straub | |
| 2012/0323211 A1 | 12/2012 | Ogle | |
| 2013/0030461 A1 | 1/2013 | Marks | |
| 2013/0144326 A1 | 6/2013 | Brady | |
| 2013/0197567 A1 | 8/2013 | Brady | |
| 2013/0226225 A1 | 8/2013 | Sachar | |
| 2013/0310871 A1 | 11/2013 | Ravish | |
| 2013/0317589 A1 | 11/2013 | Martin | |
| 2013/0345739 A1 | 12/2013 | Brady | |
| 2014/0005712 A1 | 1/2014 | Martin | |
| 2014/0005713 A1 | 1/2014 | Bowman | |
| 2014/0005717 A1 | 1/2014 | Martin | |
| 2014/0128905 A1 | 5/2014 | Molaei | |
| 2014/0155908 A1 | 6/2014 | Rosenbluth | |
| 2014/0214067 A1 | 7/2014 | Sachar | |
| 2014/0249565 A1* | 9/2014 | Laine | A61F 2/012 606/200 |
| 2014/0276922 A1 | 9/2014 | McLain | |
| 2014/0277383 A1 | 9/2014 | Sachar | |
| 2014/0324091 A1 | 10/2014 | Rosenbluth | |
| 2014/0330286 A1 | 11/2014 | Wallace | |
| 2014/0371779 A1 | 12/2014 | Vale | |
| 2015/0018859 A1 | 1/2015 | Quick | |
| 2015/0018928 A1 | 1/2015 | Sachar | |
| 2015/0018929 A1 | 1/2015 | Martin | |
| 2015/0025555 A1 | 1/2015 | Sos | |
| 2015/0032144 A1 | 1/2015 | Holloway | |
| 2015/0112376 A1 | 4/2015 | Molaei | |
| 2015/0133918 A1 | 5/2015 | Sachar | |
| 2015/0164523 A1 | 6/2015 | Brady | |
| 2015/0190155 A1 | 7/2015 | Ulm, III | |
| 2015/0238207 A1 | 8/2015 | Cox | |
| 2015/0250497 A1 | 9/2015 | Marks | |
| 2015/0265299 A1 | 9/2015 | Cooper | |
| 2015/0305756 A1 | 10/2015 | Rosenbluth | |
| 2015/0352325 A1 | 12/2015 | Quick | |
| 2015/0360001 A1 | 12/2015 | Quick | |
| 2016/0008014 A1 | 1/2016 | Rosenbluth | |
| 2016/0051733 A1 | 2/2016 | Bettinger | |
| 2016/0089228 A1 | 3/2016 | Sachar | |
| 2016/0106448 A1 | 4/2016 | Brady | |
| 2016/0106449 A1 | 4/2016 | Brady | |
| 2016/0113663 A1 | 4/2016 | Brady | |
| 2016/0113664 A1 | 4/2016 | Brady | |
| 2016/0113665 A1 | 4/2016 | Brady | |
| 2016/0143721 A1 | 5/2016 | Rosenbluth | |
| 2016/0213458 A1 | 7/2016 | Sachar | |
| 2016/0228134 A1 | 8/2016 | Martin | |
| 2016/0262790 A1 | 9/2016 | Rosenbluth | |
| 2016/0287276 A1 | 10/2016 | Cox | |
| 2016/0287844 A1 | 10/2016 | Sachar | |
| 2016/0367285 A1 | 12/2016 | Sos | |
| 2017/0007390 A9 | 1/2017 | Sachar | |
| 2017/0079672 A1 | 3/2017 | Quick | |
| 2017/0105745 A1 | 4/2017 | Rosenbluth | |
| 2017/0112513 A1 | 4/2017 | Marchand | |
| 2017/0112514 A1 | 4/2017 | Marchand | |
| 2017/0112647 A1 | 4/2017 | Sachar | |
| 2017/0119408 A1 | 5/2017 | Ma | |
| 2017/0189041 A1 | 7/2017 | Cox | |
| 2017/0265878 A1 | 9/2017 | Marchand | |
| 2017/0312069 A1 | 11/2017 | Sachar | |
| 2017/0325839 A1 | 11/2017 | Rosenbluth | |
| 2017/0333076 A1 | 11/2017 | Bruzzi | |
| 2017/0348122 A1 | 12/2017 | Sachar | |
| 2018/0008748 A1 | 1/2018 | Bettinger | |
| 2018/0049761 A1 | 2/2018 | Bashir | |
| 2018/0092652 A1 | 4/2018 | Marchand | |
| 2018/0125512 A1 | 5/2018 | Nguyen | |
| 2018/0193043 A1 | 7/2018 | Marchand | |
| 2018/0206862 A1 | 7/2018 | Long | |
| 2018/0207397 A1 | 7/2018 | Look | |
| 2018/0256178 A1 | 9/2018 | Cox | |
| 2018/0296240 A1 | 10/2018 | Rosenbluth | |
| 2018/0344339 A1 | 12/2018 | Cox | |
| 2018/0361116 A1 | 12/2018 | Quick | |
| 2019/0021751 A1 | 1/2019 | Bashir | |
| 2019/0046219 A1 | 2/2019 | Marchand | |
| 2019/0070401 A1 | 3/2019 | Merritt | |
| 2019/0110803 A1 | 4/2019 | Horowitz | |
| 2019/0110804 A1 | 4/2019 | Horowitz | |
| 2019/0133616 A1 | 5/2019 | Sachar | |
| 2019/0142444 A1 | 5/2019 | Horowitz | |
| 2019/0150959 A1 | 5/2019 | Cox | |
| 2019/0175184 A1 | 6/2019 | Hui | |
| 2019/0216476 A1 | 7/2019 | Barry | |
| 2019/0231373 A1 | 8/2019 | Quick | |
| 2019/0231508 A1 | 8/2019 | Sachar | |
| 2019/0262598 A1 | 8/2019 | Mock | |
| 2019/0321071 A1 | 10/2019 | Marchand | |
| 2019/0365395 A1 | 12/2019 | Tran | |
| 2020/0022711 A1 | 1/2020 | Look | |
| 2020/0029985 A1 | 1/2020 | Nguyen | |
| 2020/0046368 A1 | 2/2020 | Merritt | |
| 2020/0078045 A1 | 3/2020 | Wallace | |
| 2020/0107842 A1 | 4/2020 | Greenhalgh | |
| 2020/0129194 A1 | 4/2020 | Wallace | |
| 2020/0155178 A1 | 5/2020 | Culbert | |
| 2020/0170666 A1 | 6/2020 | Trosper | |
| 2020/0178991 A1 | 6/2020 | Greenhalgh | |
| 2020/0178992 A1 | 6/2020 | Wallace | |

(56) References Cited

U.S. PATENT DOCUMENTS

| | | |
|---|---|---|
| 2020/0197031 A1 | 6/2020 | Nguyen |
| 2020/0197032 A1 | 6/2020 | Wallace |
| 2020/0222171 A1 | 7/2020 | Nguyen |
| 2020/0297363 A1 | 9/2020 | Look |
| 2020/0315642 A1 | 10/2020 | Greenhalgh |
| 2020/0330117 A1 | 10/2020 | Loisel |
| 2020/0367917 A1 | 11/2020 | Teigen |
| 2020/0397957 A1 | 12/2020 | Teigen |
| 2021/0059695 A1 | 3/2021 | Harari |
| 2021/0068854 A1 | 3/2021 | Wallace |
| 2021/0106346 A1 | 4/2021 | Wallace |
| 2021/0113224 A1 | 4/2021 | Dinh |
| 2021/0128182 A1 | 5/2021 | Teigen |
| 2021/0128185 A1 | 5/2021 | Nguyen |
| 2021/0186543 A1 | 6/2021 | Wallace |
| 2021/0228222 A1 | 7/2021 | Porter |
| 2021/0228386 A1 | 7/2021 | Sachar |
| 2021/0330344 A1 | 10/2021 | Rosenbluth |
| 2021/0378694 A1 | 12/2021 | Thress |
| 2022/0000505 A1 | 1/2022 | Hauser |
| 2022/0000506 A1 | 1/2022 | Hauser |
| 2022/0000507 A1 | 1/2022 | Hauser |
| 2022/0015798 A1 | 1/2022 | Marchand |
| 2022/0022898 A1 | 1/2022 | Cox |

FOREIGN PATENT DOCUMENTS

| | | |
|---|---|---|
| CN | 103764049 | 4/2014 |
| CN | 103932756 | 7/2014 |
| CN | 104068910 | 10/2014 |
| CN | 108348319 | 7/2018 |
| CN | 110652645 | 1/2020 |
| CN | 111281482 | 6/2020 |
| CN | 106794015 B | 10/2020 |
| DE | 102017004383 | 7/2018 |
| EP | 1254634 | 11/2002 |
| EP | 1867290 | 2/2013 |
| EP | 2967824 A1 | 1/2016 |
| EP | 3169247 B1 | 5/2020 |
| GB | 1588072 | 4/1981 |
| GB | 2498349 | 7/2013 |
| JP | H6190049 | 7/1994 |
| JP | 2001522631 | 11/2001 |
| JP | 2004097807 | 4/2004 |
| JP | 2005095242 | 4/2005 |
| JP | 2005230132 | 9/2005 |
| JP | 2005323702 | 11/2005 |
| JP | 2006094876 | 4/2006 |
| JP | 2011526820 | 10/2011 |
| WO | 1997017889 | 5/1997 |
| WO | 9833443 | 8/1998 |
| WO | 9838920 | 9/1998 |
| WO | 9839053 | 9/1998 |
| WO | 9851237 | 11/1998 |
| WO | 1999044542 | 9/1999 |
| WO | 2000032118 | 6/2000 |
| WO | 2000053120 | 9/2000 |
| WO | 2002002162 | 1/2002 |
| WO | 20003015840 | 2/2003 |
| WO | 2004018916 | 3/2004 |
| WO | 2004093696 | 11/2004 |
| WO | 2005046736 | 5/2005 |
| WO | 2005113035 A2 | 12/2005 |
| WO | 2006110186 | 10/2006 |
| WO | 2007092820 | 8/2007 |
| WO | 2009082513 | 7/2009 |
| WO | 2009086482 | 7/2009 |
| WO | 2009155571 | 12/2009 |
| WO | 2010002549 | 1/2010 |
| WO | 2010010545 | 1/2010 |
| WO | 2010023671 | 3/2010 |
| WO | 2010049121 | 5/2010 |
| WO | 2010102307 | 9/2010 |
| WO | 2011032712 | 3/2011 |
| WO | 2011054531 | 5/2011 |
| WO | 2011073176 | 6/2011 |
| WO | 2012009675 | 1/2012 |
| WO | 2012011097 | 1/2012 |
| WO | 2012049652 | 4/2012 |
| WO | 2012065748 | 5/2012 |
| WO | 2012120490 | 9/2012 |
| WO | 2012162437 | 11/2012 |
| WO | 2014047650 | 3/2014 |
| WO | 2014081892 | 5/2014 |
| WO | 2014165023 A1 | 10/2014 |
| WO | 2015006782 | 1/2015 |
| WO | 2015061365 | 4/2015 |
| WO | 2015121424 | 8/2015 |
| WO | 2015189354 | 12/2015 |
| WO | 2015191646 | 12/2015 |
| WO | 2017024258 | 2/2017 |
| WO | 2017058280 | 4/2017 |
| WO | 2017070702 | 4/2017 |
| WO | 2017106877 | 6/2017 |
| WO | 2017189535 | 11/2017 |
| WO | 2017189550 | 11/2017 |
| WO | 2017189591 | 11/2017 |
| WO | 2017189615 | 11/2017 |
| WO | 2017210487 | 12/2017 |
| WO | 2018049317 | 3/2018 |
| WO | 2018080590 | 5/2018 |
| WO | 2018148174 | 8/2018 |
| WO | 2019010318 | 1/2019 |
| WO | 2019050765 | 3/2019 |
| WO | 2019075444 | 4/2019 |
| WO | 2019079121 A1 | 4/2019 |
| WO | 2019094456 | 5/2019 |
| WO | 2019222117 | 11/2019 |
| WO | 2019246240 | 12/2019 |
| WO | 2020036809 | 2/2020 |
| WO | 2021067134 | 4/2021 |
| WO | 2021076954 | 4/2021 |
| WO | 2021127202 | 6/2021 |
| WO | 2021248042 | 12/2021 |
| WO | 2022032173 | 2/2022 |

OTHER PUBLICATIONS

Friedman, "The prophylactic extraction of third molars: A public health hazard", American J of Public Health, vol. 97, No. 9, Sep. 2007, pp. 1554-1559.

Babatunde, et al. "Dry Socket: Incidence, Clinical Features, and Predisposing Factors", International Journal of Dentistry, vol. 2014, Article ID 796102, 2014, 7 pages.

Shastri, VP. "Non-Degradable Biocompatible Polymers in Medicine: Past, Present and Future" Current Pharmaceutical Biotechnology, vol. 4, 2003, pp. 331-337; p. 332, table 1, line 12.

Pubchem. CID 442424, Jun. 24, 2005, pp. 1-25 [online], [retrieved on Aug. 25, 2020]. Retrieved from the Internet <URL: https://pubchem.ncbi.nlm.nih.gov/compound/442424>.

International Search Report for PCT/US14/24158, dated Jul. 30, 2014.

Written Opinion of the International Searching Authority for PCT/US14/24158, dated Jul. 30, 2014.

International Search Report for PCT/US21/71888, dated Feb. 23, 2022.

* cited by examiner

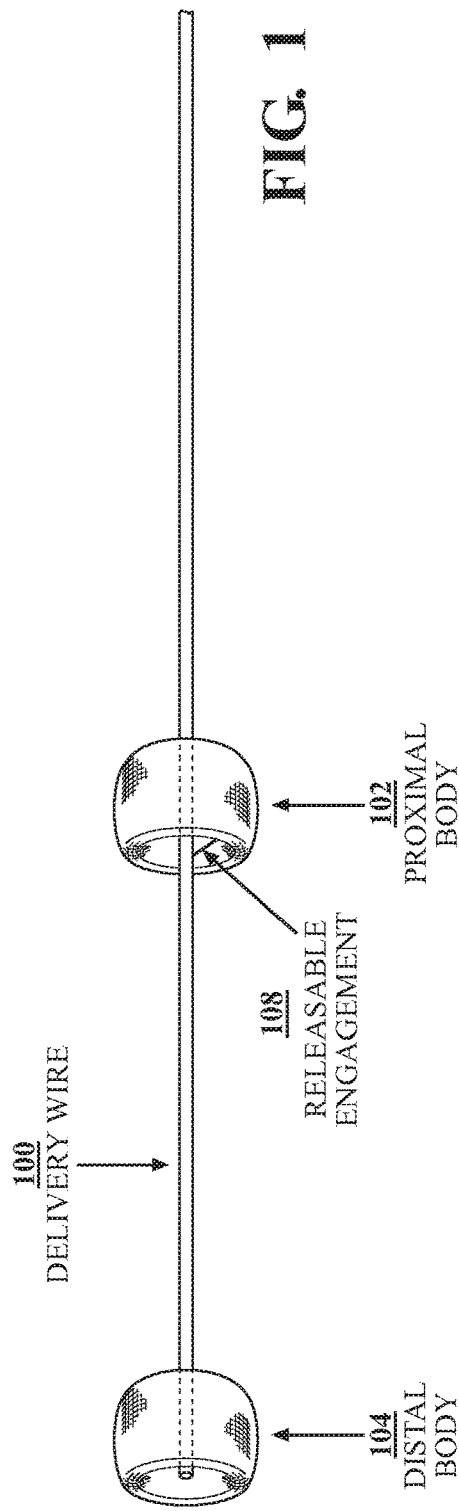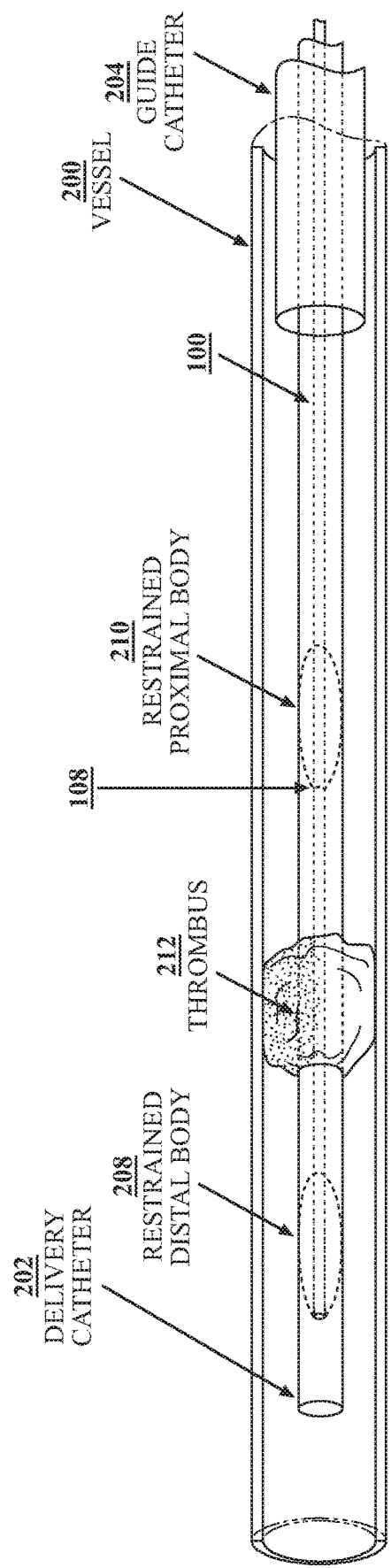

CATHETER BASED RETRIEVAL DEVICE WITH PROXIMAL BODY HAVING AXIAL FREEDOM OF MOVEMENT

CROSS-REFERENCE TO RELATED APPLICATIONS

The present application is a continuation of U.S. patent application Ser. No. 17/127,521, titled "Catheter Based Retrieval Device with Proximal Body Having Axial Freedom of Movement" and filed on Dec. 18, 2020, which is a continuation of U.S. patent application Ser. No. 16/205,632, titled "Method to Remove a Thrombus", filed on Nov. 30, 2018, and issued as U.S. Pat. No. 10,898,215 on Jan. 26, 2021, which is a division of U.S. patent application Ser. No. 15/953,131, titled "Catheter Based Retrieval Device with Proximal Body Having Axial Freedom of Movement", filed on Apr. 13, 2018, and issued as U.S. Pat. No. 10,172,634 on Jan. 8, 2019.

U.S. patent application Ser. No. 15/953,131 relies on, for priority, the following U.S. Patent Provisional Applications: U.S. Patent App. No. 62/573,006, filed on Oct. 16, 2017; U.S. Patent App. No. 62/606,993, filed on Oct. 16, 2017; U.S. Patent App. No. 62/589,613, filed on Nov. 22, 2017; and U.S. Patent App. No. 62/653,247, filed on Apr. 5, 2018.

All of the above applications are hereby incorporated by reference in their entirety.

FIELD OF THE INVENTION

The disclosure generally relates to methods and systems for the catheter-based removal of occlusions and unwanted matter from vessels, ducts and other cavities or lumens of an organism.

BACKGROUND OF THE INVENTION

Current medical devices that are used for the removal of occlusions, such as thrombi from the vessels (such as those in the brain), have limitations that reduce their effectiveness, reliability, and ease of use. For example, current devices are designed exclusively for the vascular system, and may not be used for extraction of material from ducts, ureters, urethra, or other anatomical features. Current devices are not appropriate for use in large vascular structures such as aorta, vena cava and many peripheral vascular applications, and often do not work well with calcified, organized material due to inability of the wire structures often used to compress into the embolic material prior to an attempted extraction. Current devices often have a wire structure that must incorporate into a thrombus to remove a clot and provide poor distal protection from secondary emboli during thrombus extraction due to open ended stent retriever or partial grasping of thrombus. This may result in an intended thrombectomy procedure causing distal clot embolization and occlusion of previously patent arterial branches and collaterals. Current devices may be less effective when used with associated arterial stenoses due to device collapse and tendency for a stenosis to strip and debride thrombus from device as it is retracted through the stenotic vessel segment. Current devices often require operators to choose a predetermined device length at time of device insertion, but the chosen device length might not match the size of the target thrombus once the operator is in the vessel and provided a closer view of the target thrombus.

Current catheter-based methods and systems for the removal of foreign bodies from an artery, duct, ureter or other interior physical space, often require multiple co-axial (or concentric) sleeves or delivery catheters, some of which are intended for placement on the proximal side of an occlusion, some for direction through the occlusion for placement on the distal side of the occlusion, and still others for holding inflatable balloons, thrombus removal devices and the like. The presence of multiple catheters increases manufacturing complexity and cost, in addition to increasing complexity of usage during an intervention, with greater moving parts and the required ordering of operation aligned with the function of the multiple catheters. Current catheter-based methods and systems are also manufactured and deployed in the clinical setting with a specific catheter, meaning that if during an intervention a clinician wants to deploy ("load"), for example, a retrieval device having a different size than that first deployed in a vessel, the entire catheter-based tool must be withdrawn and a new catheter-based device with the preferred diameter loaded inserted. Additional limitations of the current catheter-based systems include, but are not limited to, a reliance on fixed-diameter instrumentation and/or inflatable bodies (e.g., balloons) for encapsulation of a foreign body or occlusion. As an example, catheters using an inflatable balloon for a distal body and/or proximal body may require that an interventionist pre-select a balloon model and size prior to entering a vessel or cavity because inflatable balloons have a manufactured minimum and maximum inflation diameter. Thus, if the incorrect balloon size is selected, or the clinical setting requires flexibility in the expansion or contraction diameter of the distal or proximal bodies, the intervention may be interrupted to allow for size adaptation of equipment. Incorrect sizing may also increase the likelihood for negative clinical sequelae, such as embolization and release of occlusive matter if, for example, distal protection is lost.

Therefore, there is a need for methods and systems of thrombus, or other matter, removal in which an object targeted for removal may be dynamically surrounded by a retrieval device, rather than incorporated into the target object, wherein the retrieval device can surround the target and may be physically adjusted to match the size of the target object while within the vessel or other cavity.

SUMMARY

Provided herein are occlusion removal devices, and methods and systems of capturing and removing occlusions, thrombi, biological matter and foreign objects from anatomical systems, including the vascular system, ducts, ureters, urethra, or other anatomical features.

Embodiments of the present disclosure include an occlusion removal device comprising a first body adapted to be mounted to a delivery wire and releasably engaged to the delivery wire, wherein while engaged the first body remains fixed on the delivery wire and upon release moves axially along the delivery wire, and a second body adapted to be mounted to the delivery wire. A first proximal body may be oriented proximally to a second distal body. The proximal body and the distal body may be adapted to expand upon exiting a delivery catheter. The proximal body may be releasably engaged by a mechanically breakable connection or an electrolytically or heat disconnectable connection, the electrolytically disconnectable connection being broken upon an application of electric current to the electrolytically disconnectable connection. The proximal and distal bodies may be mesh, and may be made of nitinol.

Embodiments of the present disclosure include a method of removing an occlusion comprising inserting a guide catheter into a body lumen of a patient, and advancing a delivery catheter through the guide catheter, the delivery catheter having a delivery wire therein, the delivery wire having a proximal body and a distal body mounted to the delivery wire, the proximal body releasably engaged to the delivery wire. The delivery catheter may be advanced through the occlusion, and the distal body expanded at a point distal to the occlusion, and the proximal body expanded at a point proximal to the occlusion. The proximal body may be moved in a direction along the delivery wire such that the proximal body and the distal body surround the occlusion, and the proximal body, distal body, delivery wire, delivery catheter, and guide catheter retracted from the patient to remove the occlusion.

Embodiments of the present disclosure include a method to retrieve an occlusion in a lumen of a patient comprising inserting a delivery wire, sheathed by a delivery catheter, through the occlusion, and withdrawing the delivery catheter from a distal end of the delivery wire, wherein the withdrawal leaves the delivery wire protruding through the occlusion and expands a first body distal to the occlusion. A second body may be expanded that is attached to the delivery wire on a proximal side of the occlusion. The delivery wire may be withdrawn such that the first body is in contact with the distal side of the occlusion, and the second body may be advanced distally by advancing the delivery catheter distally until the second body contacts the proximal side of the occlusion. The occlusion may be removed from the lumen by withdrawing the first body and the second body, the delivery wire and the delivery catheter from the lumen.

Embodiments of the present disclosure include an occlusion removal system comprising a. a delivery wire comprising (i) a proximal end having an opening, (ii) a distal end, (iii) an outer surface, (iv) a lengthwise cavity, and (v) a first opening to the lengthwise cavity, the opening being in the outer surface of the delivery wire. A first tether having a proximal end and a distal end that may traverse the lengthwise cavity, the proximal end of the first tether having a length outside of the opening in the proximal end of the delivery wire and the distal end of the first tether having a length outside the opening in the outer surface of the delivery wire. A first body may be attached to the distal end of the first tether, the first body adapted to be slidably mounted to the delivery wire and releasably engaged to the delivery wire, wherein while engaged the first body remains fixed on the delivery wire and upon release moves axially along the delivery wire. In embodiments, a second tether may have a proximal end and a distal end and traversing the lengthwise cavity, the proximal end of the second tether having a length outside of the opening in the proximal end of the delivery wire and the distal end of the second tether having a length outside the second opening in the outer surface of the delivery wire.

Embodiments of the present disclosure include an occlusion removal system comprising a (i) delivery catheter (ii) a delivery wire at least partially within the delivery catheter, (iii) a tether having a proximal end and a distal end, the proximal end of the tether having a length outside of the delivery catheter, and (iv) a first body attached to the distal end of the tether, the first body slidably mounted to the delivery wire and releasably engaged to the delivery wire, wherein while engaged the first body remains fixed on the delivery wire and upon release moves axially along the delivery wire.

Embodiments of the present disclosure include an occlusion removal system comprising inserting a guide catheter into a body lumen of a patient, and advancing an access catheter through the guide catheter, advancing a delivery catheter through the access catheter, the delivery catheter having a delivery wire therein, the delivery wire having a first body mounted thereto in a fixed position at a distal end of the delivery wire. The delivery catheter may be advanced through the occlusion, expanding the first body distal to the occlusion. A second body may be loaded onto the delivery wire. The second body may be advanced over the delivery wire to the occlusion, and the delivery wire, delivery catheter, access catheter, and guide catheter may be retracted from the patient.

Embodiments of the present disclosure include an occlusion removal system comprising a first body mounted to a delivery wire and releasably engaged to the delivery wire, wherein while engaged the first body remains fixed on the delivery wire and upon release moves axially along the delivery wire. A second body may be mounted to the delivery wire, and an incorporation structure may be placed between the first body and the second body.

These and other systems, methods, objects, features, and advantages of the present disclosure will be apparent to those skilled in the art from the following detailed description of the preferred embodiment and the drawings. All documents mentioned herein are hereby incorporated in their entirety by reference.

BRIEF DESCRIPTION OF THE DRAWINGS

The disclosure and the following detailed description of certain embodiments thereof may be understood by reference to the following figures:

FIGS. 1-5 illustrate deployment stages of an embodiment of the retrieval device, with FIG. 1 showing the proximal and distal bodies deployed on a delivery wire.

FIG. 2 illustrates the pre-deployment stage of the proximal and distal bodies, where the proximal and distal bodies are restrained or unexpanded.

FIG. 3 illustrates the expanded or released position of the proximal and distal bodies from the delivery catheter.

FIG. 4 illustrates advancing the proximal body of the retrieval device axially along the delivery wire to trap and compress a thrombus.

FIG. 5 illustrates the removal of a thrombus using the deployed proximal and distal bodies of an embodiment of the retrieval device.

FIG. 7 illustrates a guide catheter positioned in proximal feeding artery with balloon deflated.

FIG. 8 illustrates the guide catheter of FIG. 7 with balloon inflated thus arresting anterograde blood flow through vessels.

FIG. 9 illustrates a delivery catheter positioned proximal to the thrombus with the delivery wire across the thrombus.

FIG. 10 illustrates a delivery catheter advanced over the delivery wire and across the thrombus.

FIG. 11 illustrates the retrieval device advanced through the delivery catheter and positioned, with the bodies still restrained, proximal and distal to the thrombus.

FIG. 12 illustrates the delivery catheter withdrawn proximally thus deploying the proximal and distal mesh bodies proximal and distal to the thrombus.

FIG. 13 illustrates the proximal body released from its engagement with the delivery wire and advanced axially along the delivery wire by advancing the delivery catheter to trap and compress the thrombus between the proximal and distal bodies.

FIG. 14 illustrates the delivery catheter with the bodies and compressed thrombus being removed as a single unit while suction is applied to the guide catheters.

FIG. 19 illustrates an advancing access catheter into a vessel.

FIG. 20 illustrates advancing the delivery catheter and delivery wire to the origin of an occlusion.

FIG. 21 illustrates temporary inflation of a balloon on a guide catheter to arrest anterograde flow.

FIG. 22 illustrates advancing the delivery wire, with the retrieval device loaded thereon, and delivery catheter across the thrombus and positioning the tip of the delivery catheter distal to the thrombus.

FIG. 23 illustrates deploying the bodies of the retrieval device and advancing the bodies device through the delivery catheter and deploying the bodies distal to the thrombus.

FIG. 24 illustrates the proximal and distal bodies drawn proximally to the thrombus and opening to a larger diameter when transitioning from M1 to M2 and in the process of being withdrawn proximally.

FIG. 25 illustrates the proximal body being moved proximally by the tether.

FIG. 26 illustrates withdrawing the thrombus towards the access catheter containing suction.

FIG. 27 illustrates removal of the thrombus using the access catheter containing suction.

DETAILED DESCRIPTION

Figure 3:
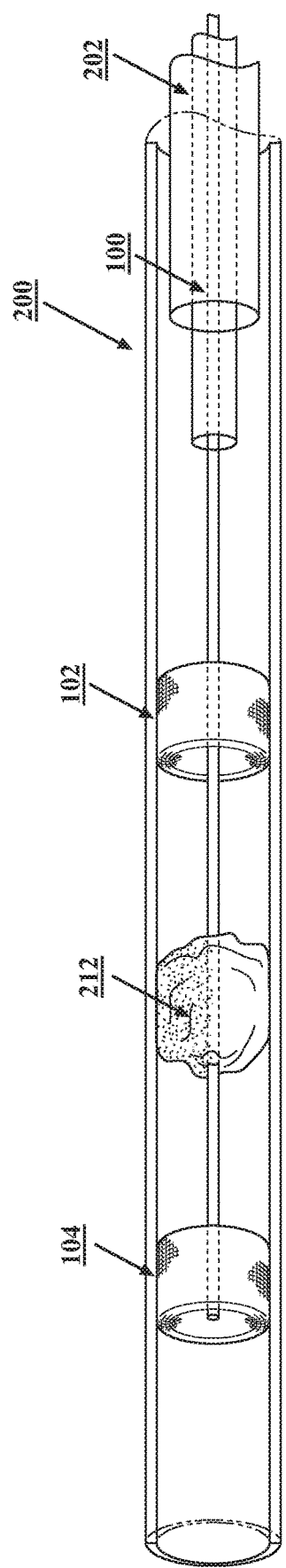

In embodiments of the present disclosure, the retrieval device, as shown in FIGS. 1 and 2, may be a catheter-delivered tool used to remove a foreign body, such as a thrombus or clot, from an artery, vein, duct, or other interior physical space. The retrieval device may be interchangeably referred to herein as "the device" or a "removal device", the "removal" or "retrieval" of the foregoing may be modified by a variety of terms such as "thrombus," "occlusion," "foreign body," etc. The retrieval device may be used as a foreign body retriever and as a thrombectomy device in the arterial and venous system. The device may be used in the vascular system and in non-vascular structures such as ureters, ducts, airways, and any other accessible space that contains a material (biologic or foreign) that necessitates removal or retrieval.

FIG. 1 depicts the deployed retrieval device with a distal body 104, which in this embodiment is a body mounted to the delivery wire 100 such that it remains in a fixed position. Referring to all embodiments disclosed herein, it should be noted that prior to deployment of the delivery wire 100, a guide wire may be used to position any element of the system disclosed herein, including a delivery catheter 202, guide catheter 204, and delivery wire 100 into the preferred position within a vessel or other interior. The "bodies" referred to herein may be a mesh, and they may be made of nitinol or other suitable expandable biocompatible material. The mesh construct of the distal 104 and proximal 102 bodies may reduce the risk of distal embolization of portions of a clot since the mesh construct may capture embolic material within its interstices. The distal body 104 may, in embodiments, have differently-sized mesh or may comprise a selectively permeable material, or it may be non-permeable. A proximal body 102 is also shown. The proximal body 102 is mounted to the delivery wire 100 and is temporarily affixed thereto such that it remains in a fixed position. The temporary affixed aspect referred to above is releasable such that upon release the proximal body 102 may move along the wire, which is referred to herein as "axial movement" along the wire, while remaining engaged to the wire 100. This aspect is referred to as being in "releasable engagement" or being "releasably engaged" to the delivery wire 100. Such releasable engagement may be achieved, for example, by using breakable connection 108, which in embodiments, may be an electrolytically or heat disconnectable connection or mechanical connection that can be selectively disconnected by the clinician. In the case of an electrolytically or heat disconnectable connection, for example, the clinician may apply a current to the connection, (in embodiments via the wire which may be conductive) wherein the electrical current breaks or melts the connection. The connection may include, without limitation, a breakable connection 108, linking a proximal body 102 to the delivery wire 100, that may be eroded and/or disintegrated through the application of electrical current. The breakable connection 108 may be preloaded onto the retrieval device in order to secure the proximal body 102 in a preferred location and/or configuration. The breakable connection may have a plurality of shapes and designs, including but not limited to a straight post extending from the delivery wire 100 to the proximal 102 or other body, a loop configuration of the breakable connection passing through the material of the proximal 102 or other body, and/or a "nail" configuration in which a straight post extends from the delivery wire to the proximal 102 or other body, wherein the post has an enlarged end, or nail head, within the body that may be eroded by the application of electric current to release the body. Embodiments of the present invention include a proximal 102 or other body that may be secured to the delivery wire 100 using more than one breakable connection 108. In an example, a proximal body 102 may be secured with multiple breakable connections, each having a different length and a different release threshold, allowing the breakable connections to be sequentially released. In embodiments, more than one proximal body may be secured to the delivery wire 100 using a breakable connection 108. Melting of a breakable connection may be caused by the application of electrical current, fluid, and/or chemical compounds. Melting may occur in a physical member that is used to secure the proximal or distal body and/or may occur within an adhesive that binds the physical member to the proximal, and/or the delivery wire 100. Breakable connection techniques and methods, including but not limited to those shown in U.S. Pat. Nos. 5,683,451, 5,855,578, 6,245,076, 8,273,116. and U.S. patent applications 20070100414A1, 20090062726A1, and 20100268251A1, may be used to release a proximal body and/or distal body, as described herein. In the case of a mechanically breakable connection, the breakable connection 108 may be made of a suture, brace, thread or other material that is able to be broken upon application of force to the breakable connection 108. in embodiments, the distal motion of a catheter, such as the delivery catheter, with a force above the threshold holding force of the breakable connection 108 may cause the connection 108 to break or release, thus allowing the body 102 to move along the wire in the manners described herein. The "bodies" referred to herein may be of various geometric shapes including a disc or sphere. In embodiments, the distal body 104 and/or proximal body 102 may be an inflatable device, including but not limited to an inflatable balloon. In embodiments, a retrieval device, as described herein, may include a distal body 104 and a proximal body 102 made of differing materials, for example a proximal body 102 may be an inflatable balloon and a distal body 104, on the same retrieval device, may be made of a mesh material. In embodiments, by adjusting the manufactured radial force, body diameter, and strength of the bodies, foreign body extraction, as described herein, may also be used for the removal of stones, pulmonary emboli, or some other type of obstruction. In embodiments, a proximal and/or distal body may have variable radial force, or stiffness across sub-regions of the body itself. For example, the upper hemisphere of a spherical body may have a difference radial force characteristic than the lower hemisphere of the body. In embodiments, the proximal and distal bodies may be substantially the same. In other embodiments, the proximal and distal bodies may be heterogeneous, having different compositions and characteristics including, without limitation, shape, size (e.g., thickness, diameter), configuration, pore size (e.g., mesh pore size), coating, or some other differing characteristic. In embodiments, the proximal and/or distal bodies may have anti-platelet, or some other type of, coatings to reduce adhesion and provide a less thrombogenic environment during clinical application. The proximal and/or distal bodies, and any material (e.g., wires) between these bodies, may be coated with control release agents including, but not limited to, thrombolytic agents.

The "delivery wire" 100 referred to herein may be a wire or a hypo tube. The delivery wire 100 may not require a coaxial system of catheters as disclosed herein in embodiments.

The "delivery catheter" 202 referred to herein may be referred to as a microcatheter, and may form a plurality of shape configurations based on the clinical application in which it is used, for example, which type of vessel the delivery catheter is used within, the vessel size, the vessel shape, or some other application characteristic. In embodiments, a delivery wire and/or hypo tube may be used within a microcatheter. For purposes of this disclosure, the microcatheter 202 is commonly called a "delivery catheter", although it should be understood that the terms can be used interchangeably.

Referring to FIG. 2, prior to deployment of the distal 208 and proximal 210 bodies (which are shown as being restrained or in their unexpanded form and thus having different reference numerals from the FIGS. 1, and 3-5) the delivery catheter 202 surrounds the delivery wire and restrains both bodies 208, 210. In embodiments, a guide catheter 204 is navigated into place, in embodiments, over a guide wire, said guide wire in some embodiments being removed. The delivery catheter 202 may be passed through an object, such as a thrombus or clot 212, the bodies 208, 210 may be released from the delivery catheter 202 either by retracting the delivery catheter 202 or advancing the wire 100, such that expandable bodies are no longer restrained by the delivery catheter 202. The distal body 104 remains fixed to the delivery wire 100, but the proximal body 102 (once released from its releasable engagement) can freely move along its axis and longitudinally along the delivery wire 100 when pushed by the delivery catheter 202. Also, the delivery wire 100 "pushing" the body (210 or 102 once expanded) must be understood as relative pushing. That is, the retraction of the delivery wire 100 while the delivery catheter 202 is kept in place may serve to move the proximal body 102 axially along the wire. The term "pushing" as is used herein will refer to both forms of movement mentioned above. Once the proximal and distal bodies are positioned adjacent to both sides of the clot (which has been referred to herein as "surrounded" or "surrounding" the clot) by movement of the proximal body 102, the clot may be removed by retrieving the device from the cavity and pulling the clot free. The terms "clot," "thrombus," "occlusion," "occlusive substance" and "foreign body" may be used interchangeably herein.

In embodiments, the freedom of movement of the proximal body 102 on the delivery wire 100 axially may allow for the compression of the occlusive substance and obviate the need for pre-measuring or estimating the required distance between the distal and proximal bodies prior to entering the vessel 200; sizing may take place in situ within the vessel 200 upon the interventionist encountering it.

In embodiments of the present disclosure, the retrieval device may consist of a distal body 104 and a proximal body 102, each of which in embodiments may be collapsible geometric forms. Although the distal and proximal bodies are presented for diagrammatic purposes as spherical, the distal and proximal bodies may also be other geometric forms such as a disc, cone, oblong-shaped form, etc. As mentioned above, the distal and proximal bodies may be a mesh in structure. The mesh cell size may be manufactured to have different sizes based on factors such as the expected properties of the target foreign matter to be removed, such as the density of the matter. The distal body 104 is mounted on a delivery wire 100 such that it remains fixed. In embodiments, the mounting of the proximal body 102 occurs by running the wire through one of the mesh opening. In other embodiments, the proximal body 102 itself may have an opening through which the wire may pass. In either case of mounting the proximal body 102, the body is able to slide along the wire in an axial direction along the wire. This may be referred to herein as "slidably mounted". In some embodiments, the distal body 104 may be slidably mounted in the way described above. As described above, the proximal body may be detachable (thus releasably engaged) using mechanical, electrolytic or some other type of control release format. In embodiments, the proximal body 102 will be slidable along the wire one released while the distal body 104 remains fixed. In other embodiments, both the proximal and distal bodies may be releasably engaged and thus slidable or movable along the delivery wire 100. Still in other embodiments, the proximal body 102 may be comprised of multiple bodies, and the distal body 104 may be comprised of multiple bodies. The mesh material of the distal and proximal bodies may have advantages over other material types, including but not limited to inflatable balloons. Inflatable material may be susceptible to rupture, such as that caused by over inflation. The clinical setting may also be associated with complications related to the use of inflatable balloons within a lumen. For example, a calcified thrombus may increase the risk of balloon rupture. In another example, if an occlusion itself includes metallic material, this may also increase the risk of rupture or other malfunction of an inflatable balloon. Rupture of a balloon may in turn increase the risk of an air embolus forming within the vessel or cavity of intervention. In embodiments, the mesh material of the distal and proximal bodies may allow for the bodies to expand upon release to the diameter and configuration of the cavity in which it is placed, such as a vessel 200 in which a thrombus 212 is located. Such meshes may be made of a shape memory substance such as nitinol. For example, a body made of nitinol mesh may expand to a first dimension outside of a vessel 200 or catheter, but may be designed to expand to a continuum of smaller dimensions than the first dimensions corresponding to different lumen sizes. In this way the bodies may fit the unique variations in diameter found in a lumen at the point of release and/or point of placement near an occlusion, such as a thrombus. Mesh material may also allow for improved distal flow during an intervention. The irregularity and/or texture of the expanded mesh material may facilitate the mesh material becoming entangled or otherwise incorporated with a clot or occlusive substance, thereby increasing adhesion of the distal and/or proximal body with the occlusion and facilitating its removal.

Figure 4:
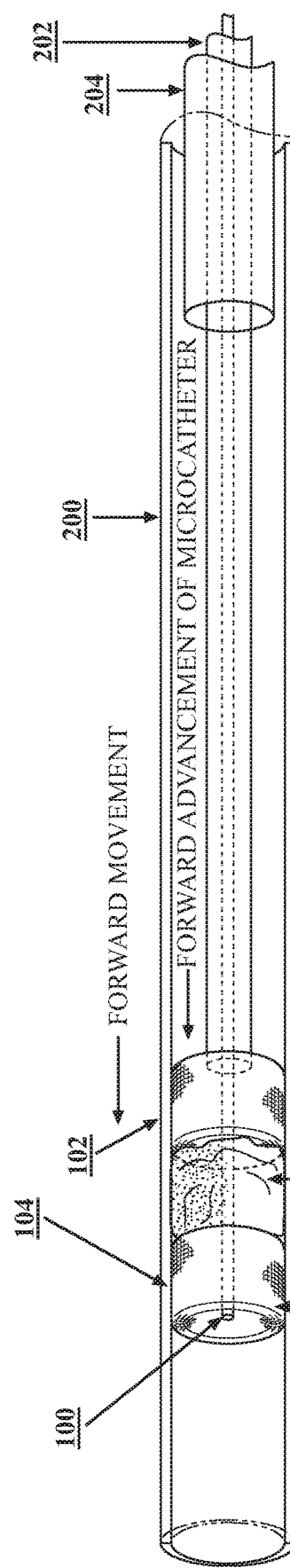
Figure 5:
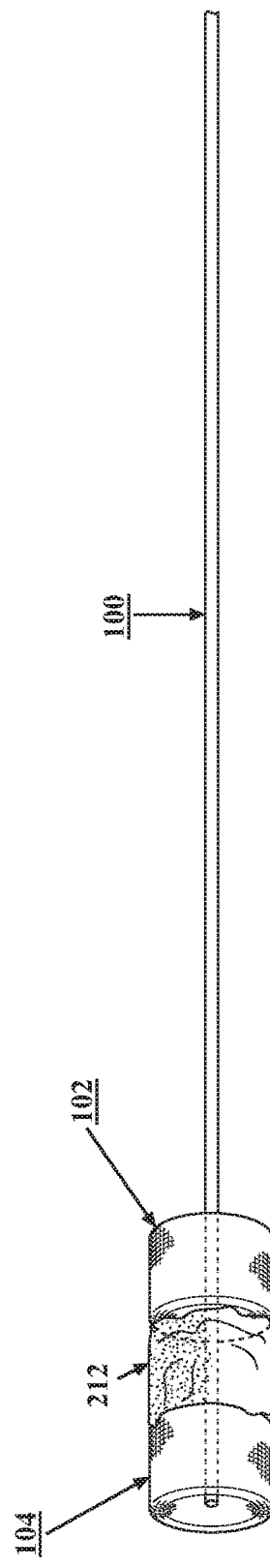

In embodiments, when the proximal body 102 is released, it may be free to move/slide on its axis along the delivery wire 100 in a longitudinal and/or rotational fashion. Referring to FIG. 3 when the distal body 104 is placed distal to the target thrombus 212 for retrieval and the proximal body 102 is placed proximal to the thrombus 212, the distal and proximal bodies will straddle and contain the thrombus 212 intended for removal from the vessel. The proximal body 102 may now be advanced in the direction of the thrombus 212 in a variety of mechanical fashions. As shown in FIG. 4, a coaxially placed microcatheter, also referred to herein as a "delivery catheter" 202, may be pushed forward (once the proximal body is released) and used to physically advance the proximal body 102 to ultimately capture and compress the thrombus 212. Alternatively, the delivery catheter 202 may be used to hold the proximal body 102 in a fixed position while the delivery wire 100 is withdrawn thus moving the fixed distal body 104 towards the proximal body 102 and ultimately capturing and compressing the thrombus 212. As shown in FIG. 5, once the thrombus 212 is captured/compressed between the distal body 104 and the proximal body 102, the entire retrieval device may be removed from the patient via withdrawal of the delivery wire 100 by, for example, withdrawing the proximal and distal bodies with the compressed material back to, and against, the delivery catheter and then removing the delivery catheter, bodies and compressed material through the guide catheter. Once this is removed, the guide catheter may be withdrawn from the vessel.

Figure 6:
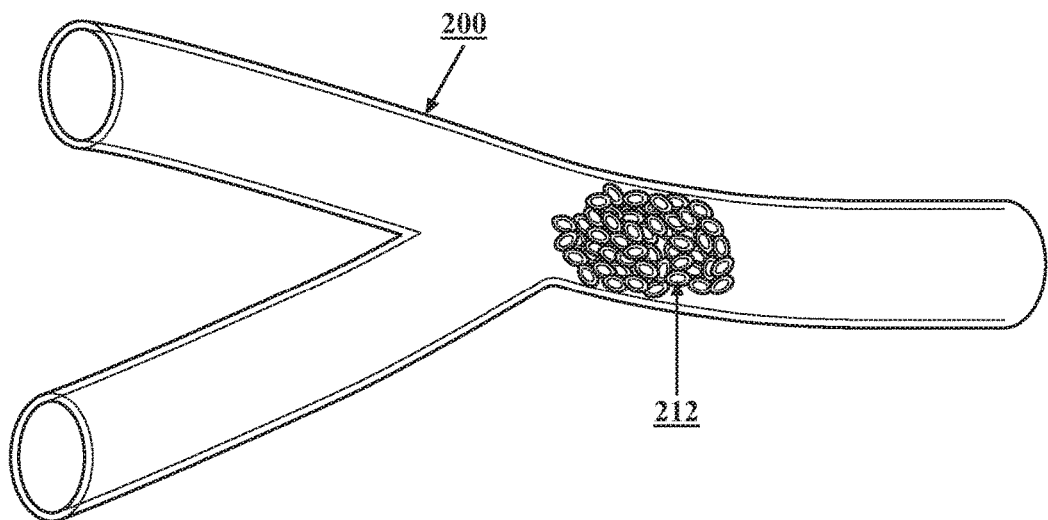
FIGS. 6-14 illustrate deployment stages of an embodiment of the retrieval device, with FIG. 6 showing a thrombus lodged in an artery.
Figure 7:
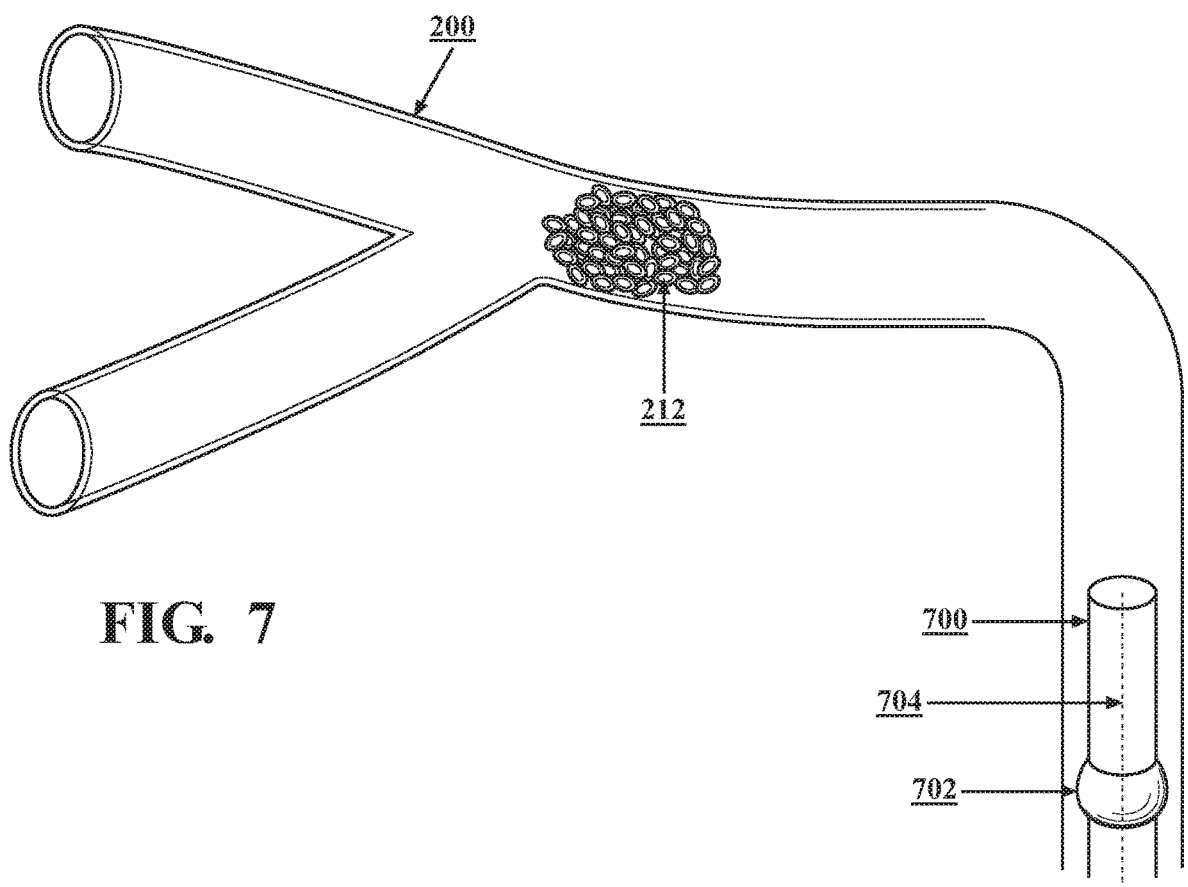
Figure 8:
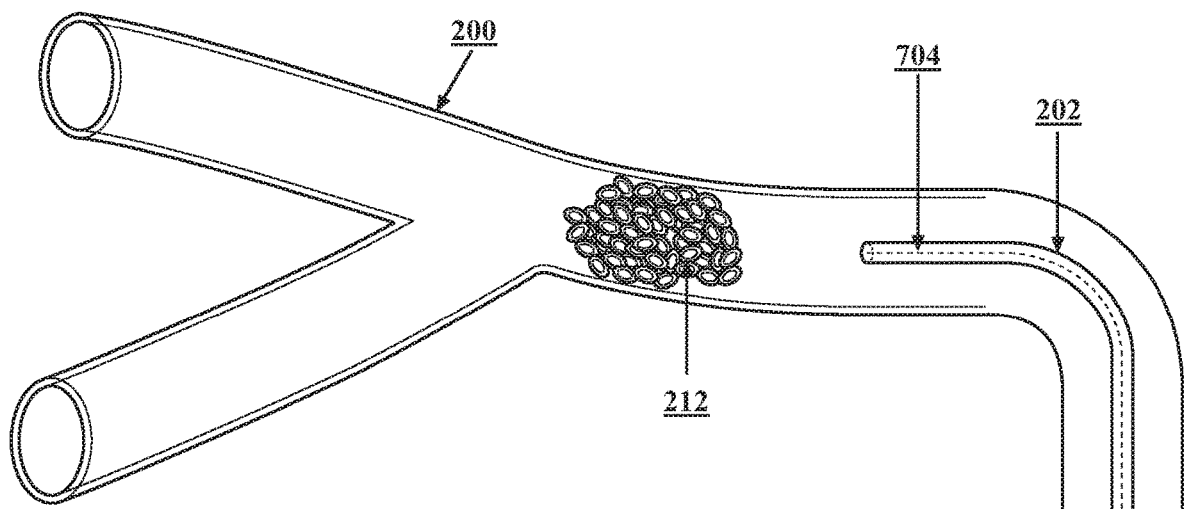
Figure 9:
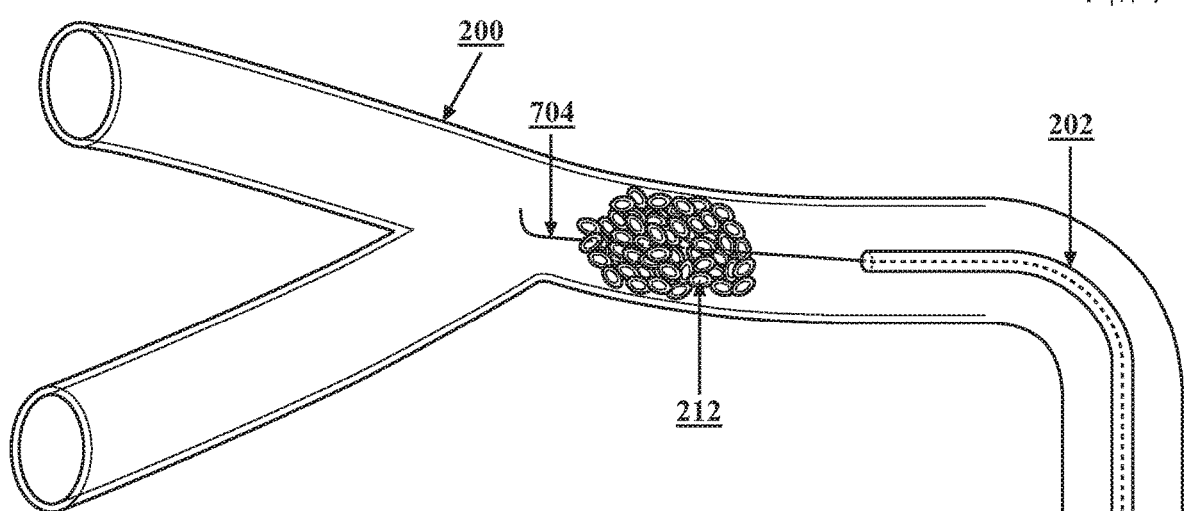
Figure 10:
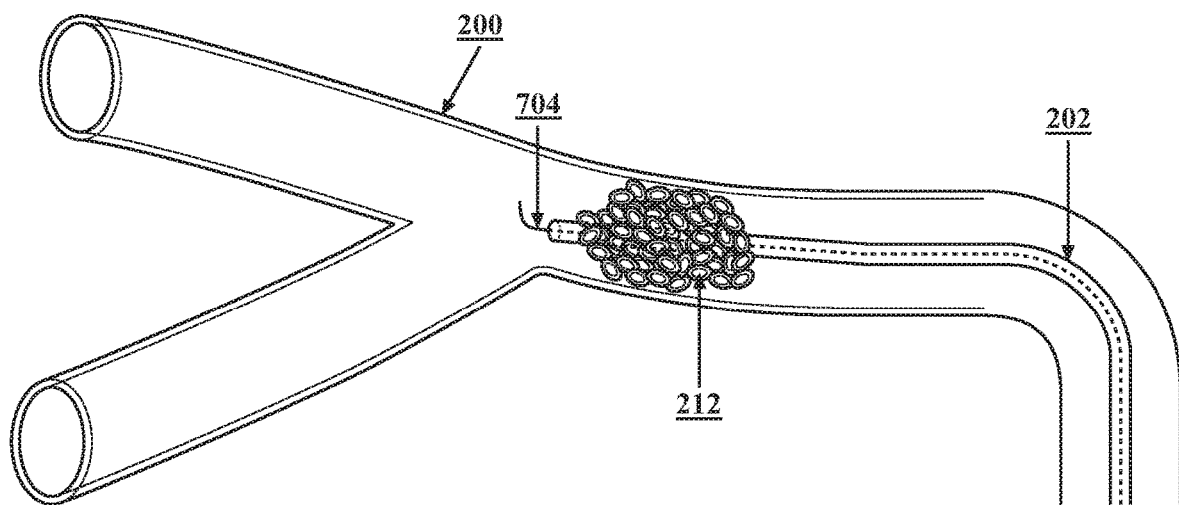
Figure 11:
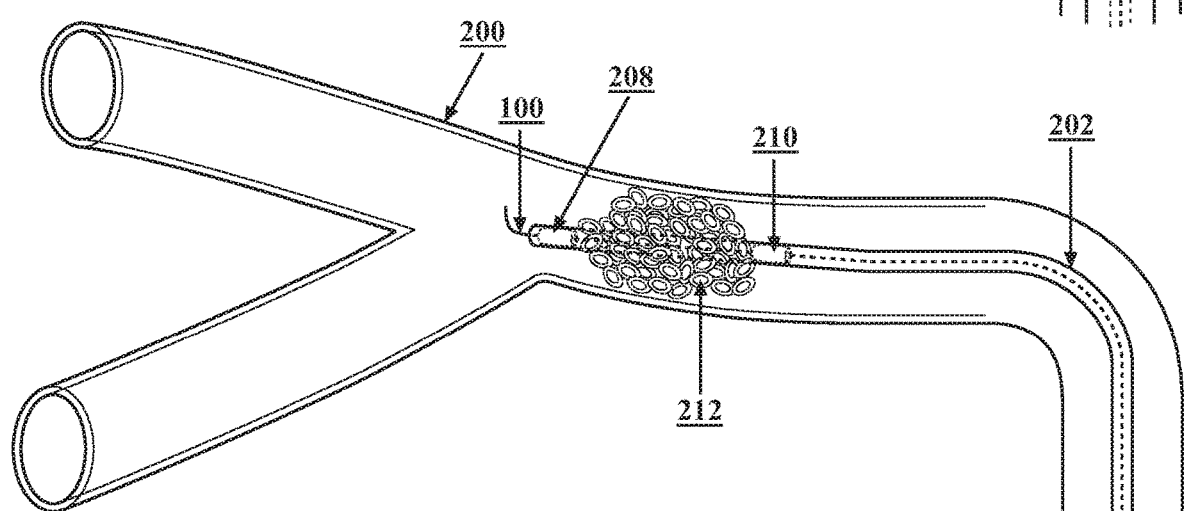
Figure 12:
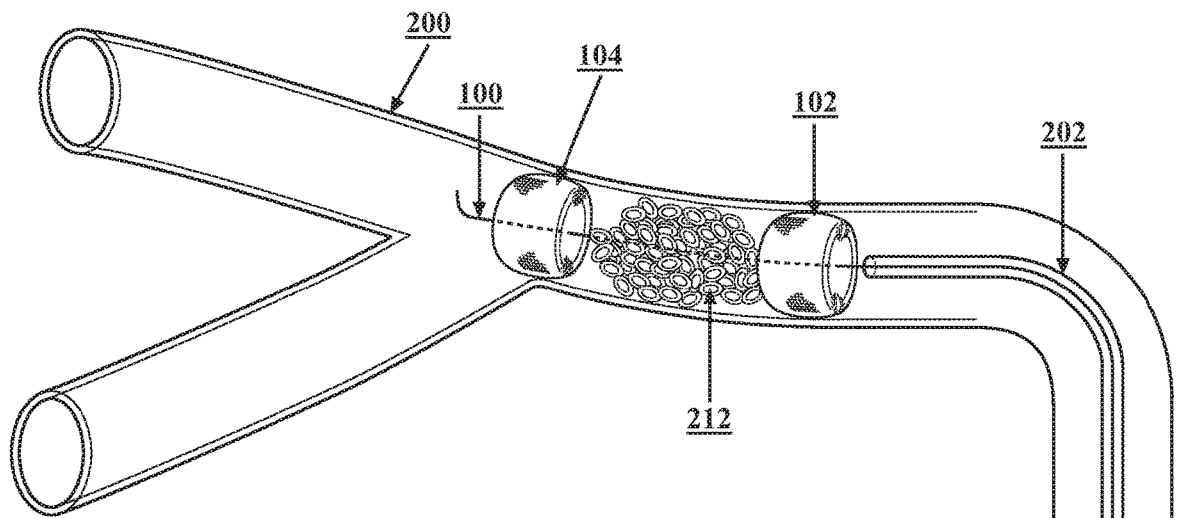
Figure 13:
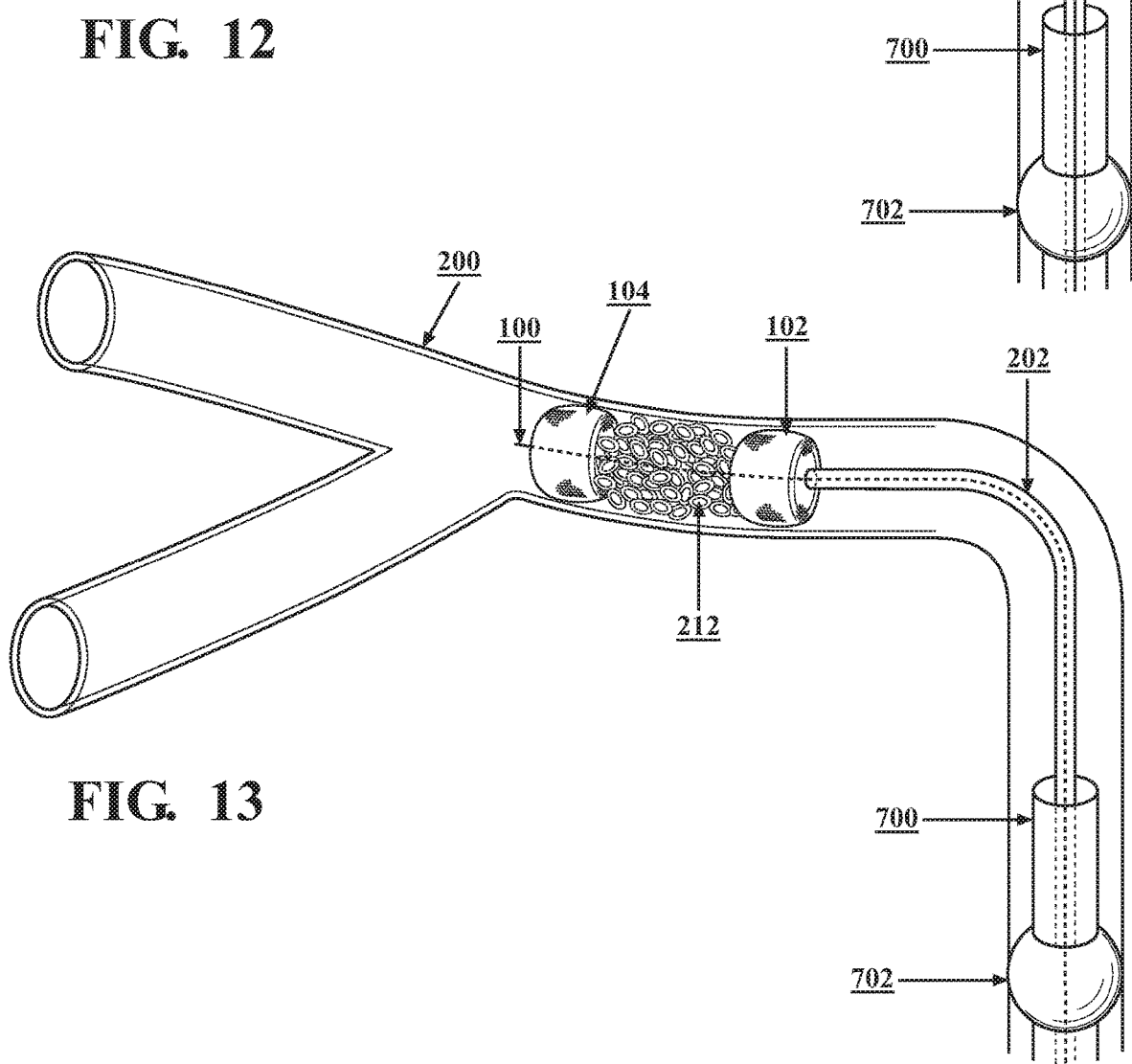
Figure 14:
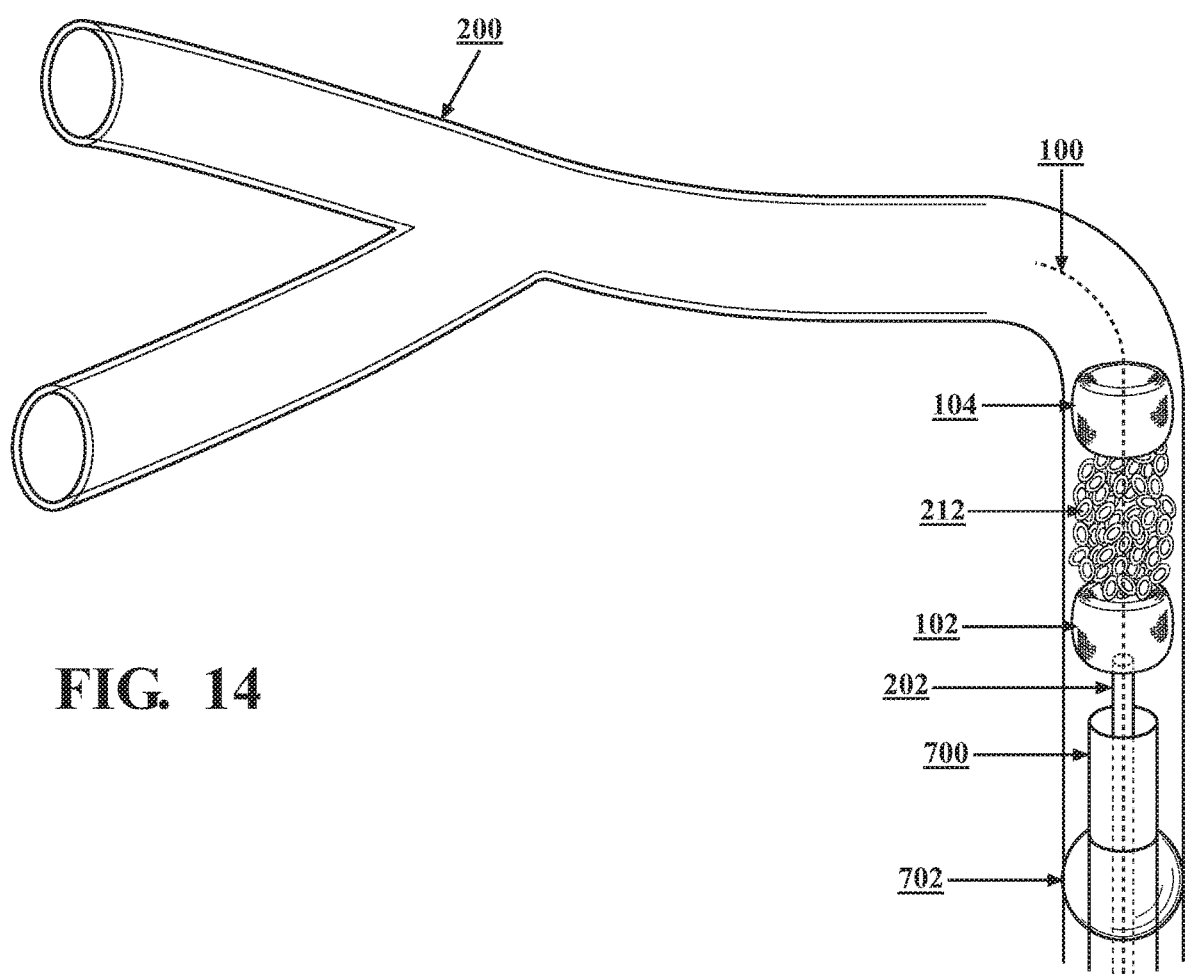

In embodiments of the present disclosure, the retrieval device may be employed as part of the removal of an occlusive object or substance from a human vessel, such as performing arterial thrombectomy. This procedure may include the following generalized steps. FIG. 6 shows an occlusion in the proximal left internal carotid artery (ICA). FIG. 7 shows an embodiment having a guide catheter 700 with a balloon 702 ("balloon catheter"). In embodiments, suction may be applied through the guide catheter 700, in effect utilizing the guide catheter 700 as a suction catheter, as a given intervention may require. The balloon 702 is deflated an inserted into the ICA over a guide wire 704. FIG. 8 shows a delivery catheter 202 advanced through the balloon catheter over the guide wire 704, which has been advanced. FIG. 9 shows a guide wire 704 being advanced through and distal to the occlusion 212. FIG. 10 shows the delivery catheter 202 being advanced through and distal to the occlusion over the guide wire 704. The guide wire 704 is then removed (not shown) and FIG. 11 shows the retrieval device (delivery with distal 208 and proximal 210 bodies mounted on a delivery wire 100 as described herein) inserted into the delivery catheter 202 and still retrained (unexpanded) in the delivery catheter 202. In FIG. 12 the delivery catheter 202 has been withdrawn (moved relative to the delivery wire 100) such that the proximal 102 and distal 100 bodies expand on either side of the occlusion 212. The proximal body 102 having been released is then advanced distally (shown in FIG. 13) by force of the delivery catheter 202 (either by pushing the delivery catheter 202 or by pulling the delivery wire 100 while restraining the position delivery catheter 202). FIG. 14 shows withdrawal of the retrieval device from the ICA, balloon 702 still inflated to arrest anterograde flow.

The retrieval device may remove both organized and unorganized thrombi since, in embodiments, the bodies of the retrieval device do not need to be incorporated into the thrombus 212 to affect its removal. The retrieval device may also remove calcified, atherosclerotic material since, in embodiments, the bodies of the retrieval device do not need to be incorporated into the material to affect its removal. The retrieval device may be used centrally and peripherally by selecting the appropriate diameter and characteristics of the bodies, such as appropriate radial force or stiffness, appropriate shape, whether the bodies are substantially identical or homogenous, mesh opening size in the bodies, and the like.

The methods, system and apparatus, as described herein, may have a plurality of sizes loaded within a common catheter, and a clinician may self-load, for example, different and/or additional proximal bodies, as described herein, rather than having to fully replace a deployed catheter for a second catheter-based device and system. This may reduce manufacturing costs and improve intervention efficiency.

Figure 15:
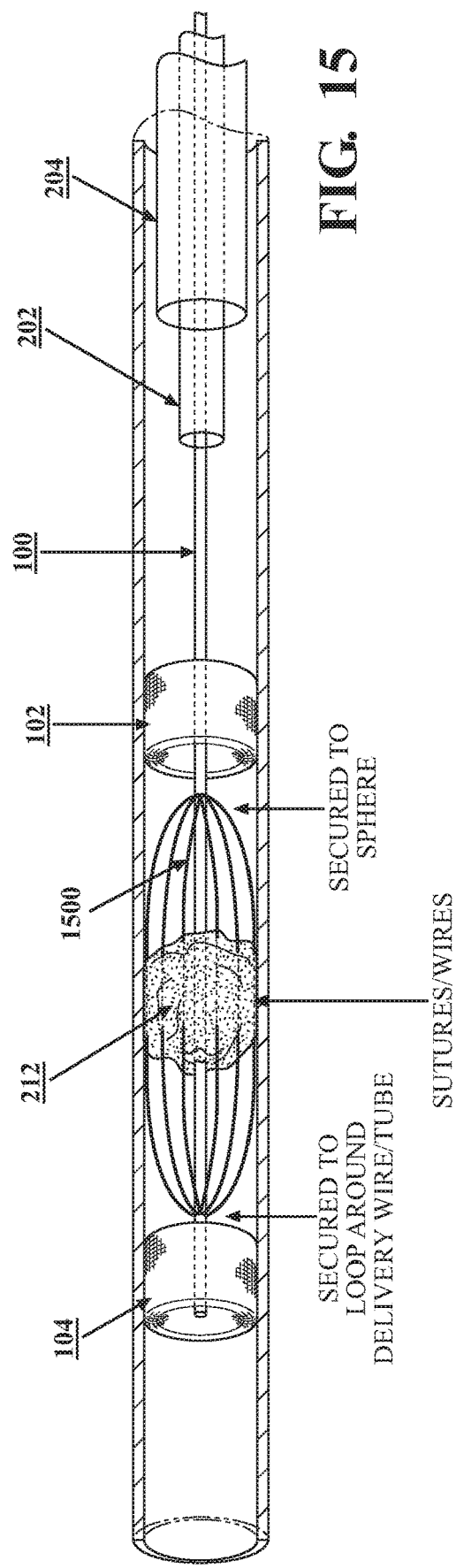
FIG. 15 illustrates an embodiment having an active segment having a section spanning the length of a thrombus, and a delivery segment containing incorporation structure that is suture material between the proximal and distal bodies.
Figure 16:
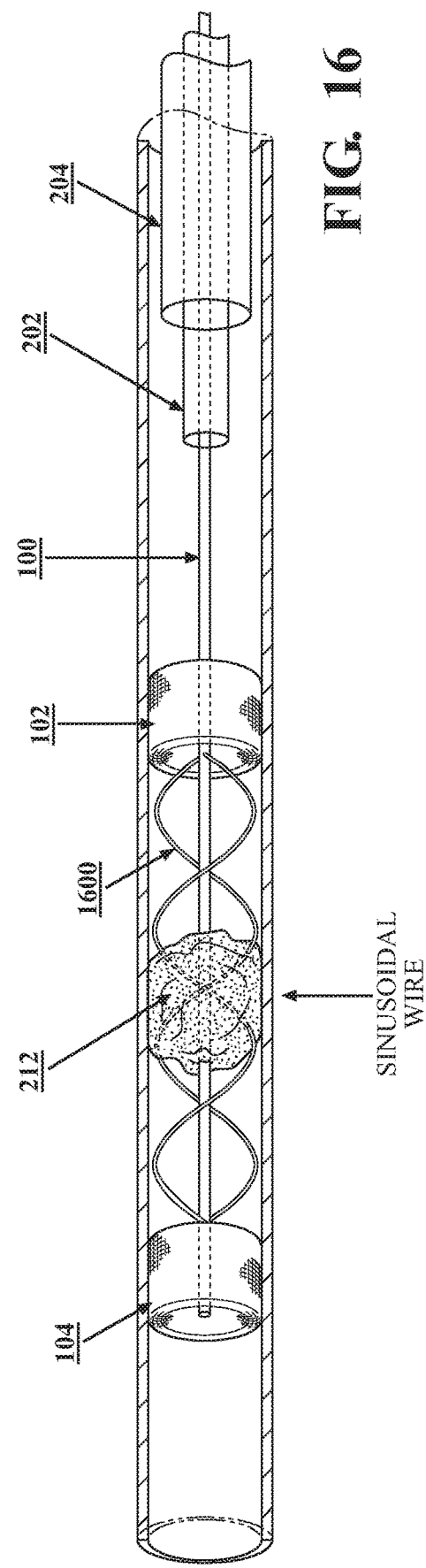
FIG. 16 illustrates an active segment having a section spanning the length of a thrombus, and a delivery segment containing incorporation structure that is collapsible sinusoidal wire material between the proximal and distal bodies.

FIGS. 15 and 16 show embodiments having a structure to incorporate into the thrombus 212, referred to herein as an "incorporation structure". In some embodiments, the incorporation structure is part of the delivery wire 100, in others it is separate. Referring to FIGS. 15 and 16, the delivery wire 100 (which in all embodiments disclosed herein may be a hypo tube) comprises a segment having characteristics different from that of the main segment of the delivery wire 100, or a structure mounted to the delivery wire 100 that may expand. In the case where the incorporation structure is part of the delivery wire 100, the segment will be referred to herein as the "active segment" while the remainder of wire will be referred to as the "delivery segment". The active segment is the segment having a section intended to span the length of the thrombus 212. In embodiments, the active segment comprises a cross-sectional shape that differs from the delivery segment. In embodiments, the delivery segment contains a suture material 1500 between the proximal 102 and distal 100 bodies. The suture material 1500 gathers and moves along the delivery wire 100 as the proximal body 102 is advanced. Once the proximal body 102 is in position, the suture material 1500 will be gathered in the area between the two bodies which will enhance incorporation characteristics of the active area. Note that the active area in the above example is the area between the two bodies, which in this case, has suture material 1500 gathered therebetween. As mentioned above, in embodiments the incorporation structure can be an additional expandable structure between the proximal 102 and distal 100 bodies that expands and incorporates into the thrombus 212. The incorporation structure may comprise other mechanisms to enhance thrombus-incorporation, such as flanges, hooks, sutures, sinusoidal wire 1600, or some other material configuration.

In embodiments, the delivery wire 100 may include a distal body 104 that may be affixed, mounted, adhered or otherwise connected to a delivery wire 100 or hypo tube as described herein. Prior to deployment, such as a thrombectomy, the distal body 104 may be affixed, mounted, adhered or otherwise connected to the delivery wire 100 or hypo tube in a collapsed or compressed state. Compression of the distal body 104 may be provided by the delivery catheter 202, and/or multiple catheters which surround the distal body 104 and delivery wire 100 (as described herein). Once the delivery catheter 202 is inserted through an object, such as a thrombus, the distal body 104 may be released from inside the delivery catheter 202 as described herein, thus expanding. Following removal of the delivery catheter 202, suction may be applied to the thrombus or other blockage. (It is to be noted that a suction step, as described herein, may be applied to any of the embodiments of this disclosure, and may be applied through the guide catheter, access catheter, specialized suction catheter, or some other type of catheter). In an example, the Seldinger technique may be initiated using a large bore suction catheter that is advanced over the delivery wire 100 (or a guide wire) and positioned proximal to the thrombus 212, with the distal body 104 distally positioned to the thrombus. Suction may be applied to remove all or a portion of the thrombus. The positioning of the distal body 104, on the distal side of the thrombus, may be used to retract the thrombus in the direction of the suction device, thereby increasing the effectiveness of the suction device in removing the thrombus. The distal body 104 may also provide distal protection from distal embolization during the suction device's placement and/or during the suctioning procedure. Note that in the above example, a proximal body has not yet been included in the procedure. There are situations and thus embodiments where an optional proximal body 102 may be added to the procedure, for example, by slidably mounting a proximal body 102 to the delivery wire 100. As such, in embodiments the inclusion of a proximal body 102 is optional.

In some clinical scenarios the suction procedure may result in only a partial removal of the thrombus 212 or other obstruction. In such scenarios, mechanical removal of the thrombus 212, using a distal body and an added proximal body 102, may be advantageous and/or required. Following the application of suction within the guide catheter 700, a proximal body 102 may be added to the delivery wire 100, where this proximal body 102 is proximal to the thrombus 212 or other obstruction. Once the proximal body 102 is placed on the delivery wire 100, it may be advanced towards the distal end of the delivery wire 100 by advancing the delivery wire 100. In another example, the proximal body 210, in a restrained position, may be advanced towards the distal end of the delivery wire 100 using a hypo tube that is placed within the delivery catheter 202 over the delivery wire. As the hypo tube is pushed towards the distal end of the delivery wire 100, the proximal body 210 may be moved axially to a desired location. Once the proximal body 210 is in the desired physical position, relative to the thrombus 212 or other obstruction, the proximal body 210 may be released from inside the delivery catheter 202 to form the expanded proximal body 102 in a manner already descried herein. The coaxially placed hypo tube may be pushed forwards and used to physically advance the proximal body 102 to ultimately capture and compress the thrombus 212. Once the thrombus 212 is captured/compressed between the distal body 104 and the proximal body 102, the entire retrieval device may be removed from the body via coaxially placed catheters/tubes thus permitting removal of the thrombus 212 from its prior resting place within the vessel.

Figure 17A:
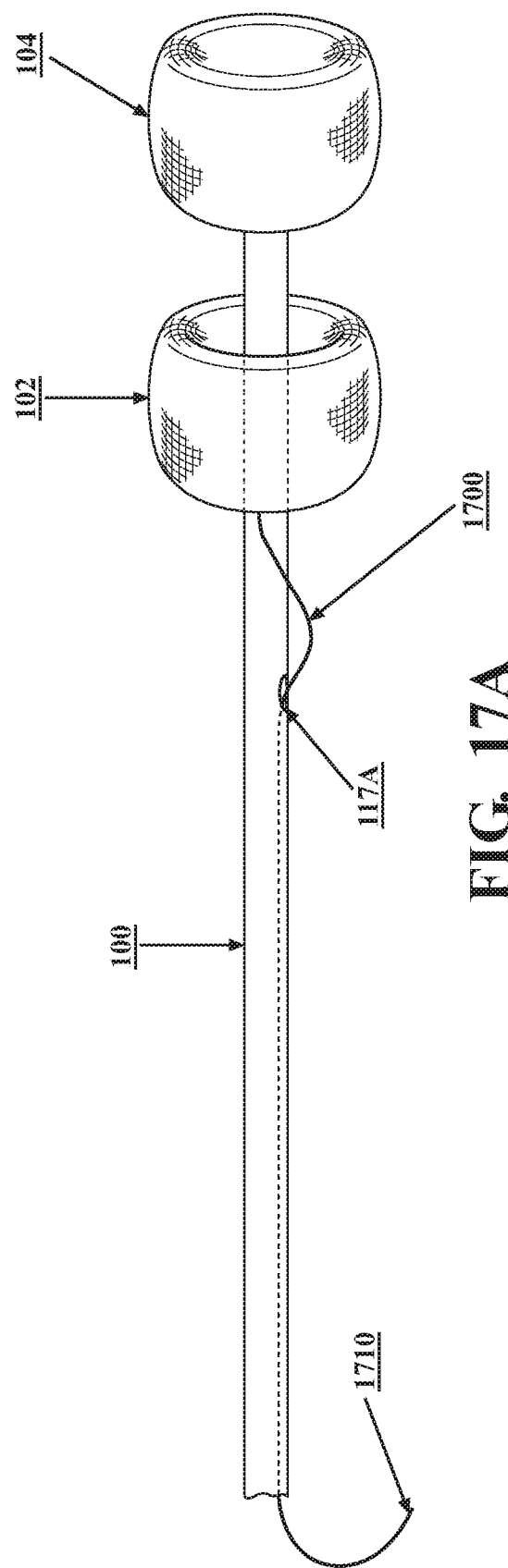
FIG. 17A illustrates the retrieval device with a single tether arrangement attached to the proximal body.
Figure 17B:
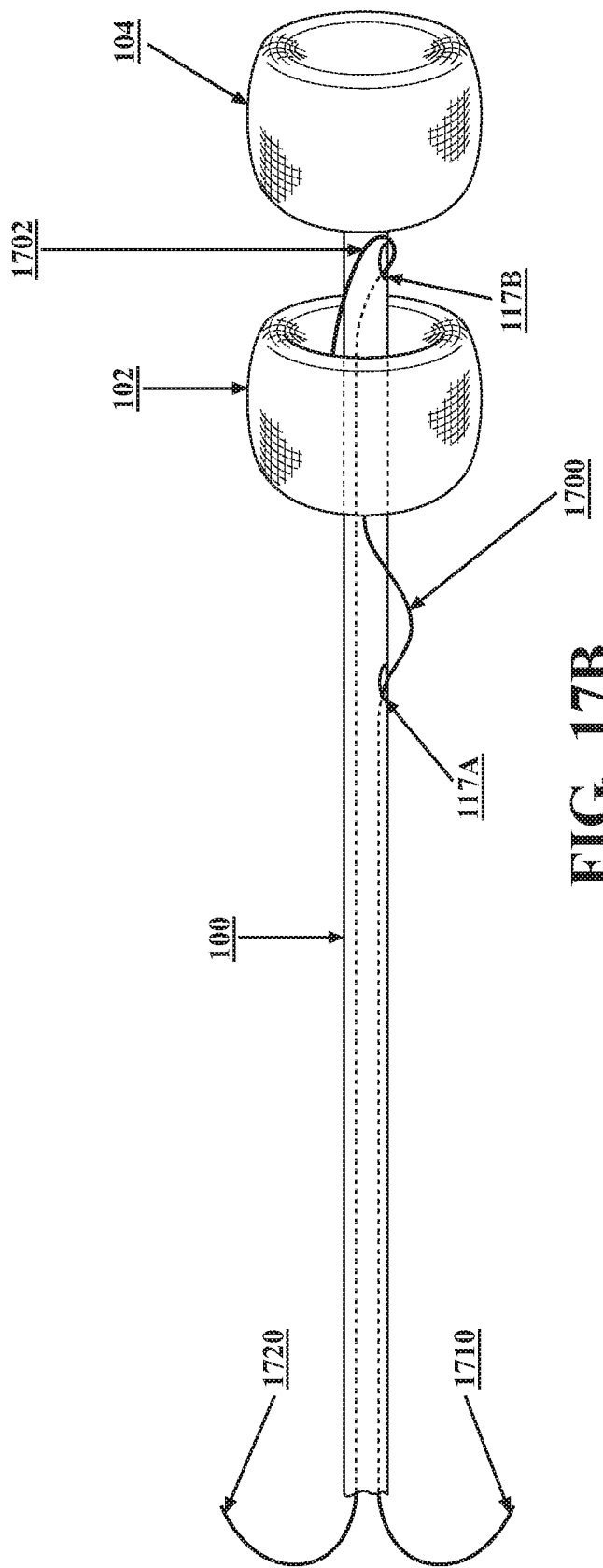
FIG. 17B illustrates the retrieval device with a double tether arrangement attached to the proximal body.

Referring to FIGS. 17A and 17B, the proximal body may be moved along the delivery wire via application of force to a tether or multiple tethers. As shown in FIG. 17A, a single proximal tether 1700 may be attached to the proximal body 102, the proximal body 102 being slidably mounted and in releasable engagement to a delivery wire (or hypo tube), as described herein. The proximal tether 1700 may be pulled to move the proximal body back, proximally along the wire 100 after the proximal body 102 has been released and positioned in the manner described herein. The proximal tether 1700 may run parallel and within the delivery catheter (not shown) or, as shown in FIG. 17A, the proximal tether 1700 may run within a hollowed-out portion of the delivery wire or hypo tube and emerge through an opening 117A. The proximal end 1710 of the proximal tether 1700 is accessible to the interventionist who can pull it to pull back, proximally to the proximal body 102 at least to the point adjacent to the opening 117A.

FIG. 17B shows a two-tether embodiment. As with the embodiment shown in FIG. 17A, the tethers may run parallel and within the delivery catheter (not shown) or, as shown in FIG. 17B, the proximal tether 1700 and distal tether 1702 may run within a hollowed-out portion of the delivery wire or hypo tube and emerge through openings 117A and 117B, where the proximal tether 1700 emerges from opening 117A and the distal tether 1702 emerges from opening 117B. Movement of the proximal body via the proximal tether, in the proximal direction, is the same as mentioned above. In this embodiment, the interventionist can pull the end of the distal tether 1720 to move the proximal body 102 adjacent to the opening 117B, which results in a distal movement of the proximal body 102 without the need for distal movement via the delivery catheter as described herein.

Figure 18:
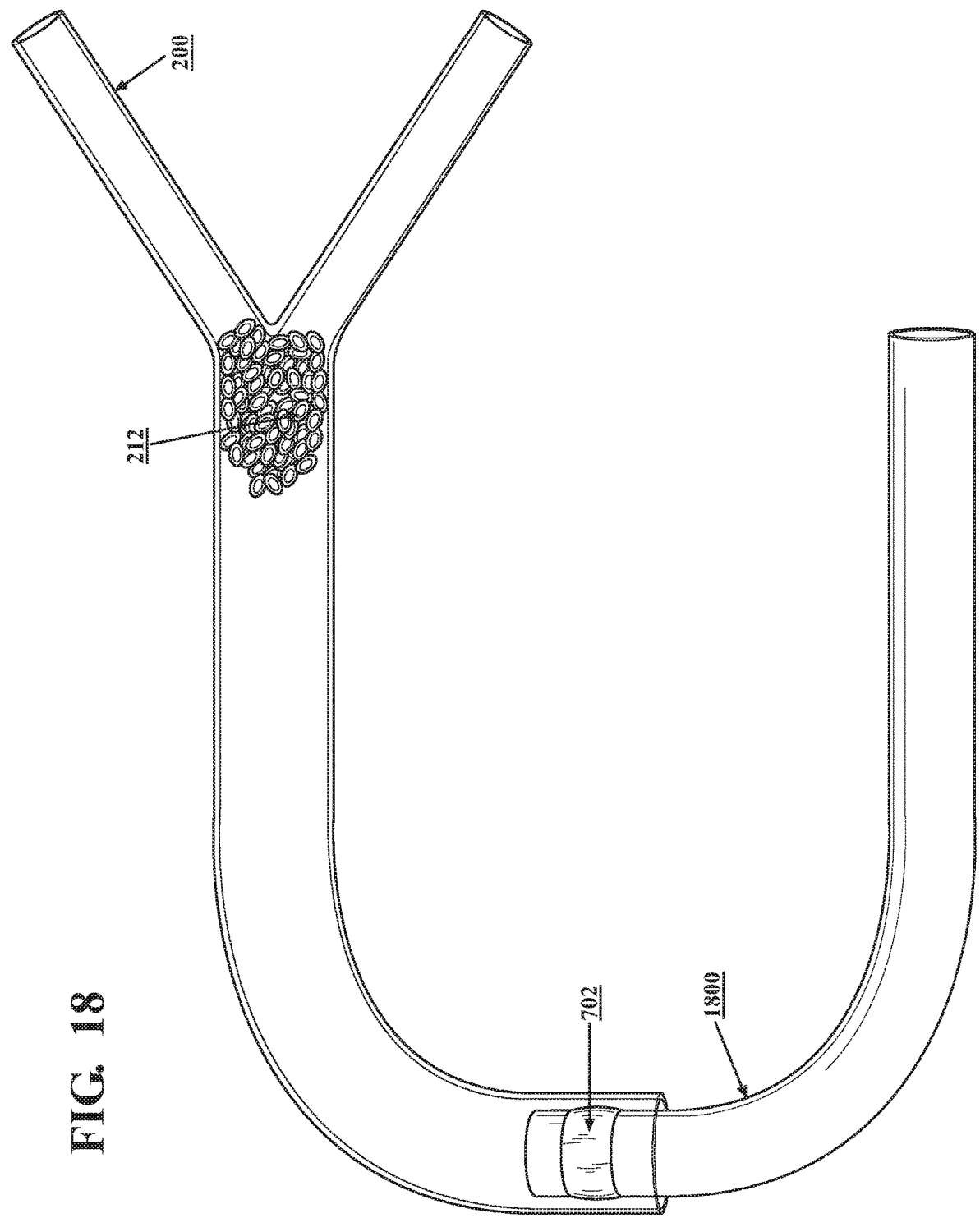
FIGS. 18-27 illustrate deployment stages of and embodiment with FIG. 18 showing the placement of a temporary balloon occlusion guide catheter into common carotid artery.
Figure 19:
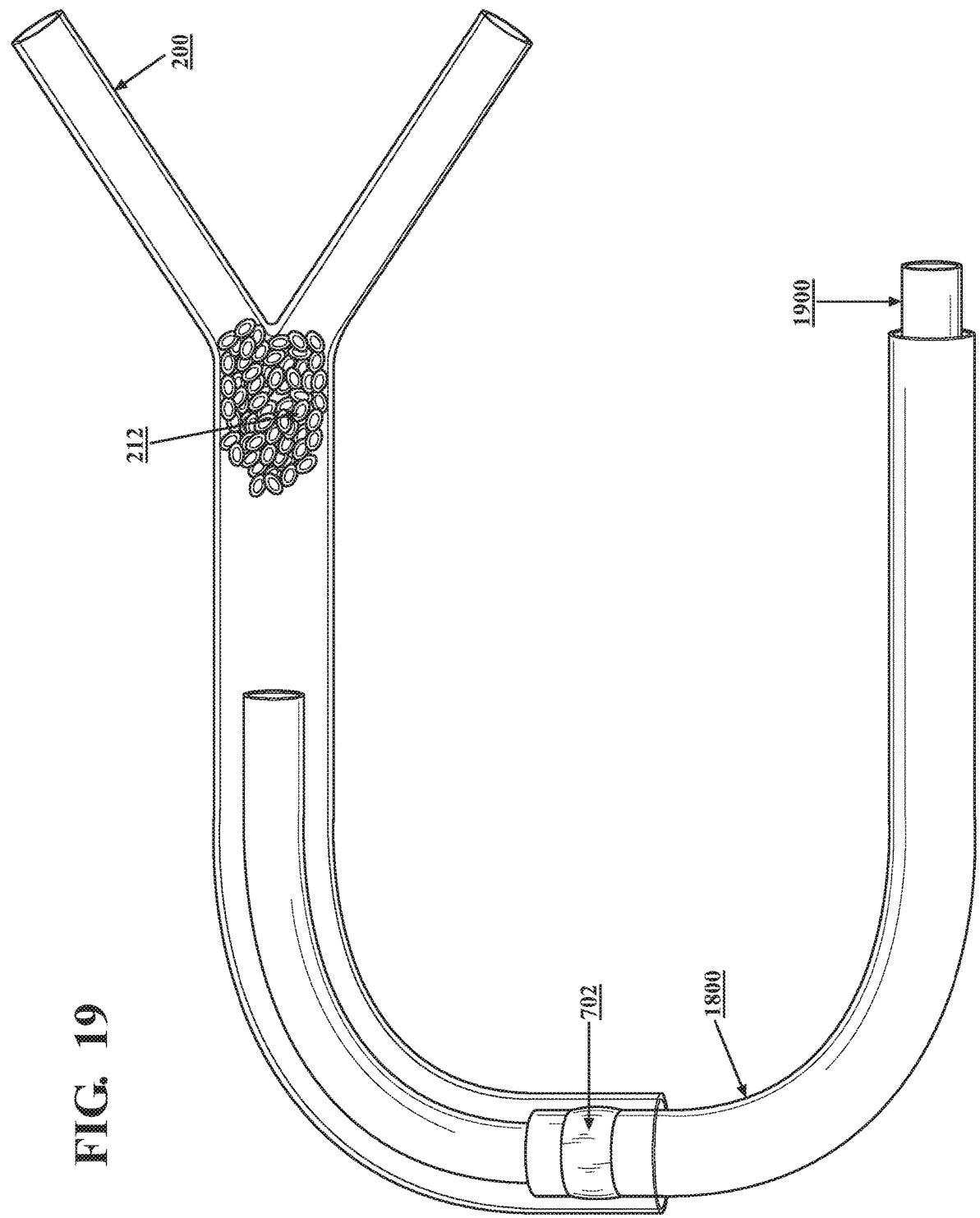
Figure 20:
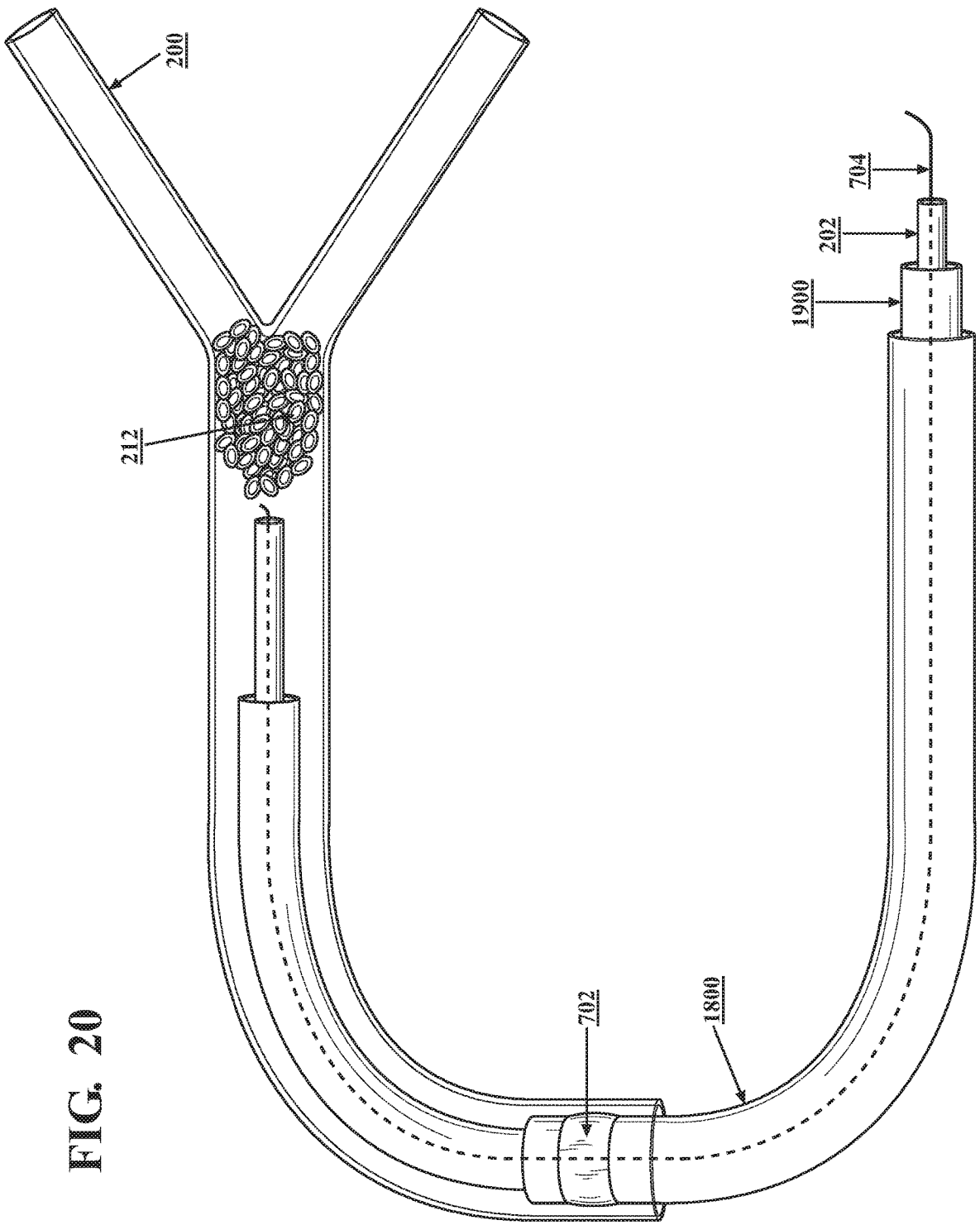
Figure 21:
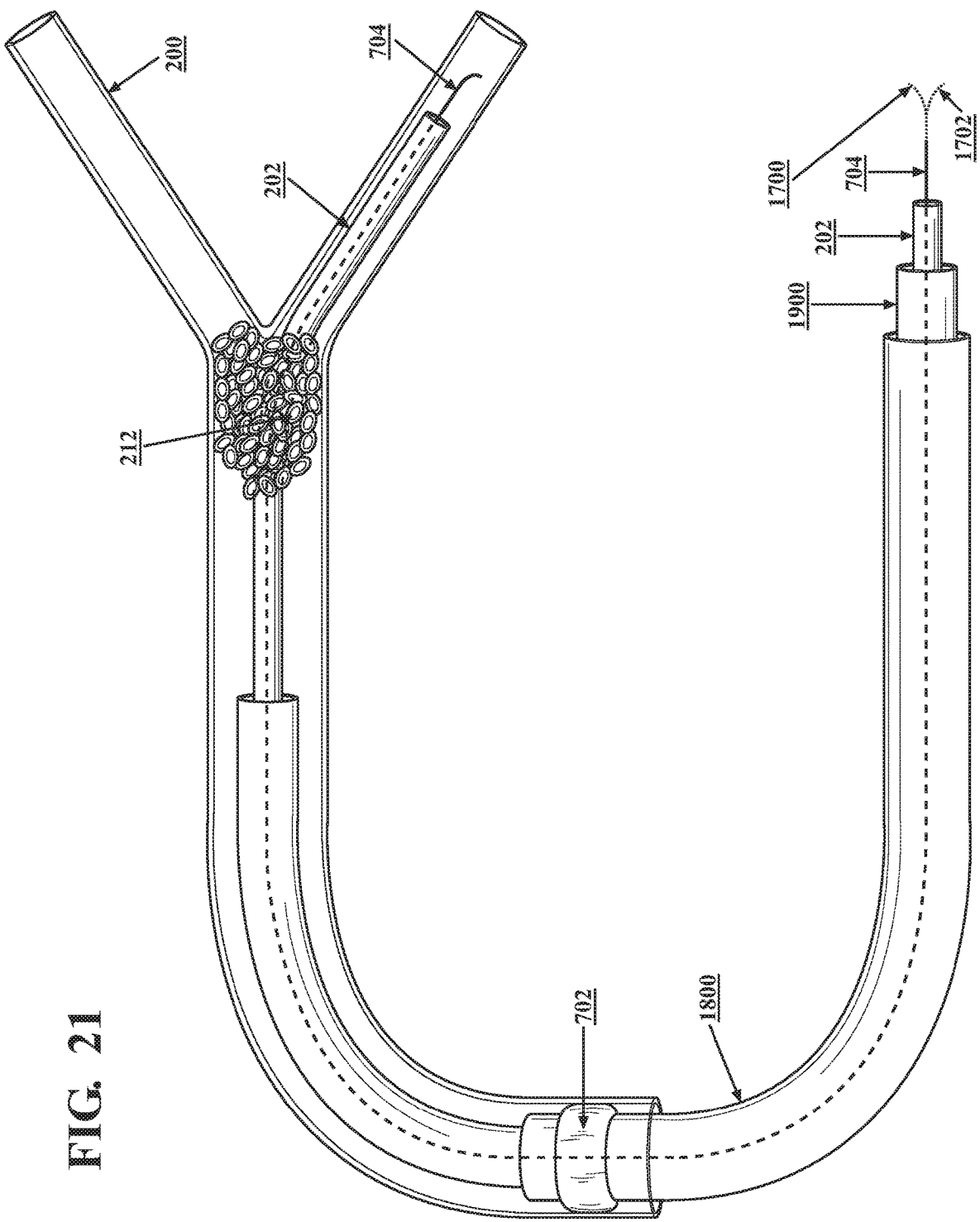
Figure 22:
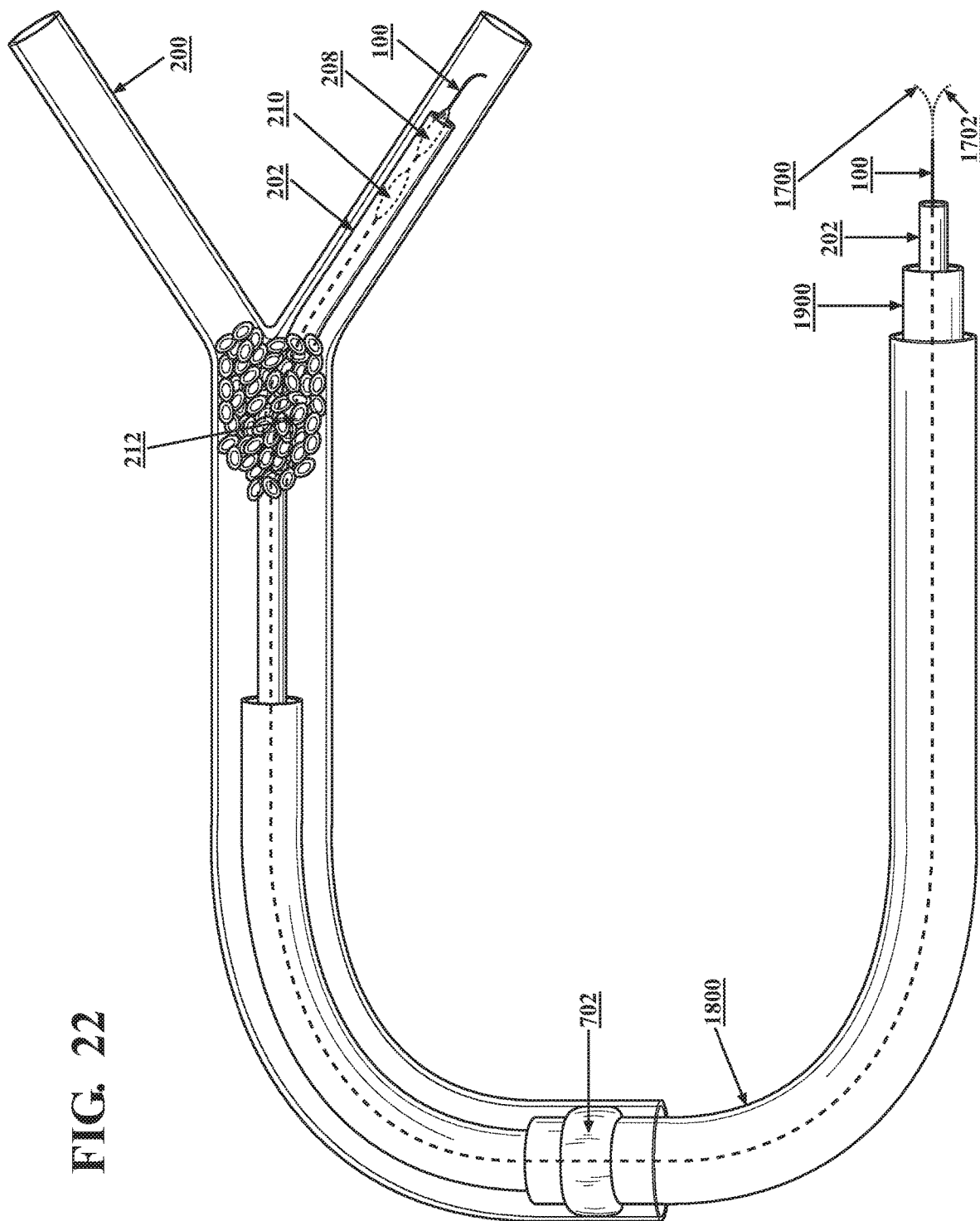

In addition to the steps of deployment mentioned above, the following steps may also or alternatively be followed for using the retrieval device in embodiments. FIG. 18 shows the common carotid artery (CCA) having an occlusion therein 212. A guide catheter 1800 having a flow arrest balloon 702 is inserted into the CCA (in embodiments over a guide wire). FIG. 18 shows the flow arrest balloon 702 as deflated. FIG. 19 shows the advancement of an access catheter 1900 distally through the guide catheter 1800 (in embodiments over a guide wire (not shown)). FIG. 20 shows the distal advancement of a delivery catheter 202 via a guide wire 704 to the origin of the inclusion (i.e., the base of the thrombus 212). FIG. 21 shows the flow arrest balloon 702 being temporarily inflated to arrest anterograde flow in the CCA as well as the delivery catheter 202 being advanced distal to the occlusion 212 via the guide wire 704 and, in this case, in M1. The guide wire 704 is removed (not shown). The delivery wire 100 with restrained proximal 210 and restrained distal 208 bodies thereon is inserted into and through the delivery catheter 202 with the tip emerging the delivery catheter as shown in FIG. 22. In this example, the delivery wire 100 has within it a proximal tether 1700 and a distal tether 1702.

Figure 23:
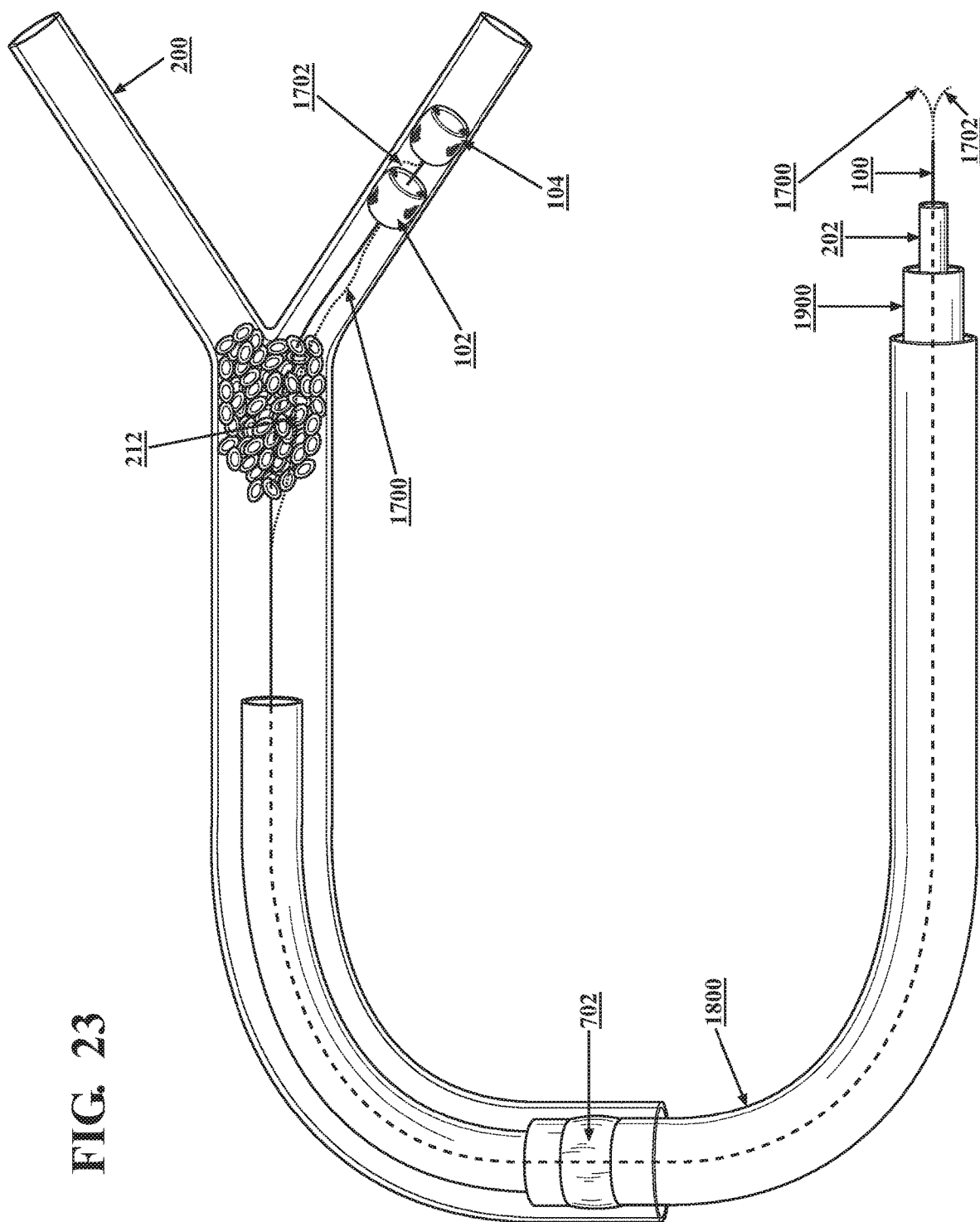

In FIG. 23, the proximal 102 and distal 104 bodies are deployed distally to the occlusion 212, the deployment being in the manner described herein. The delivery catheter 202 is withdrawn from patient to increase open luminal area in access catheter 1900, which allows for better suction when suction is applied to access catheter 1900. FIG. 23 also shows the proximal tether 1700 and the distal tether 1702, as described herein, attached to the proximal body 102. FIG. 23 also shows the deflation of flow arrest balloon 702 on the guide catheter 1800 to end flow arrest. Due to mesh construct of the proximal 102 and distal 104 bodies which are now deployed, anterograde flow into vessels will be reestablished with protection (established via the expanded proximal 102 and distal 104 bodies) from distal embolization of occlusion when flow is reestablished. Suction may be applied to the access catheter 1900 at this point. The proximal body 102 may be released from its releasable engagement 108 as described herein, while the distal body 104 remains fixed to the wire.

With both the proximal 102 and distal 104 bodies providing protection (most commonly initially in an M2 branch for an M1 occlusion or covering the M1 bifurcation for an ICA terminus) an interventionist may slowly pull the delivery wire 100 in a proximal direction. This will draw both bodies proximally (see FIGS. 23-25). The proximal 102 and distal 104 bodies will open to a larger diameter when they transition from M1 to M2 and in the process of being withdrawn proximally will begin the thrombectomy process (see FIG. 25).

Figure 24:
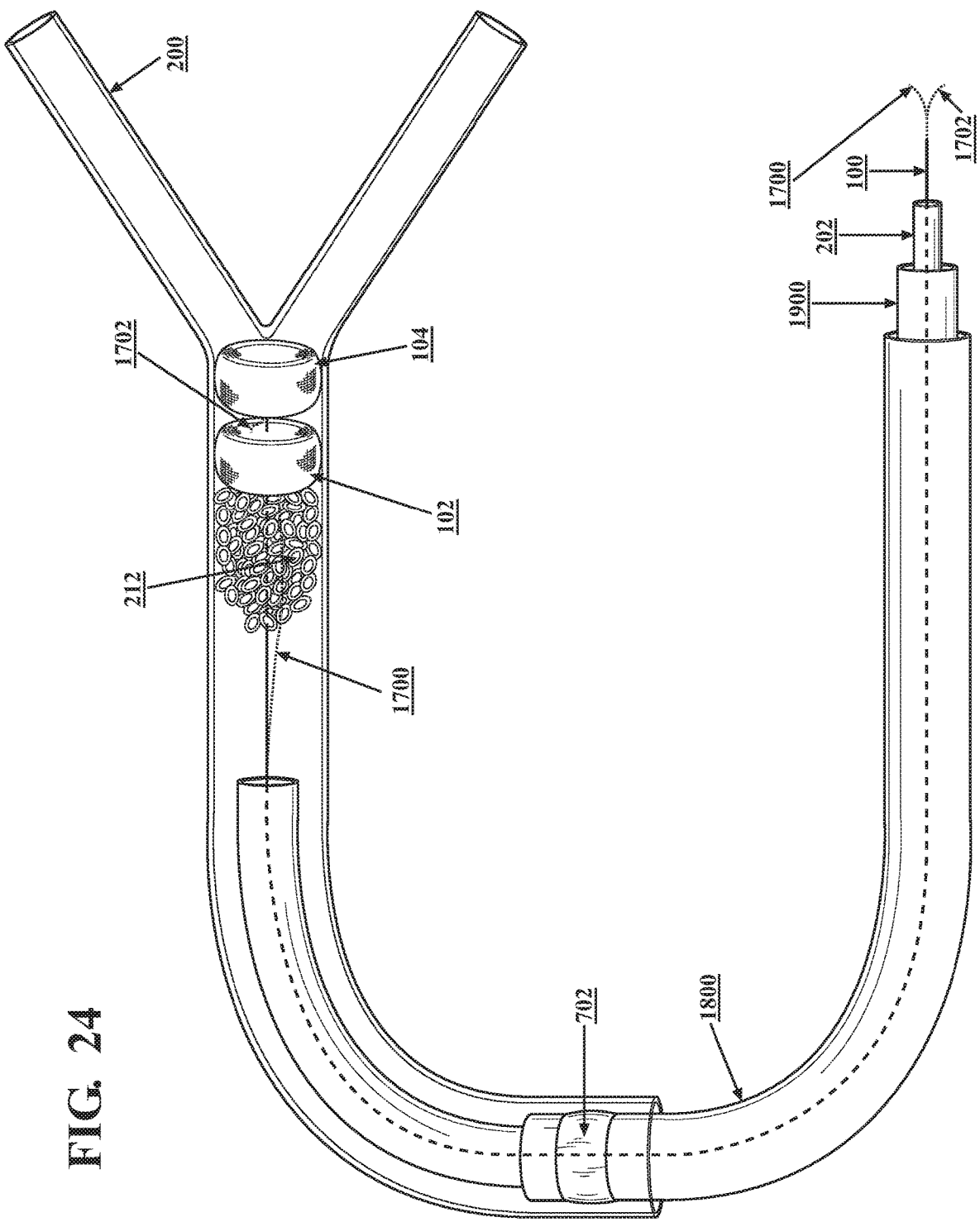
Figure 25:
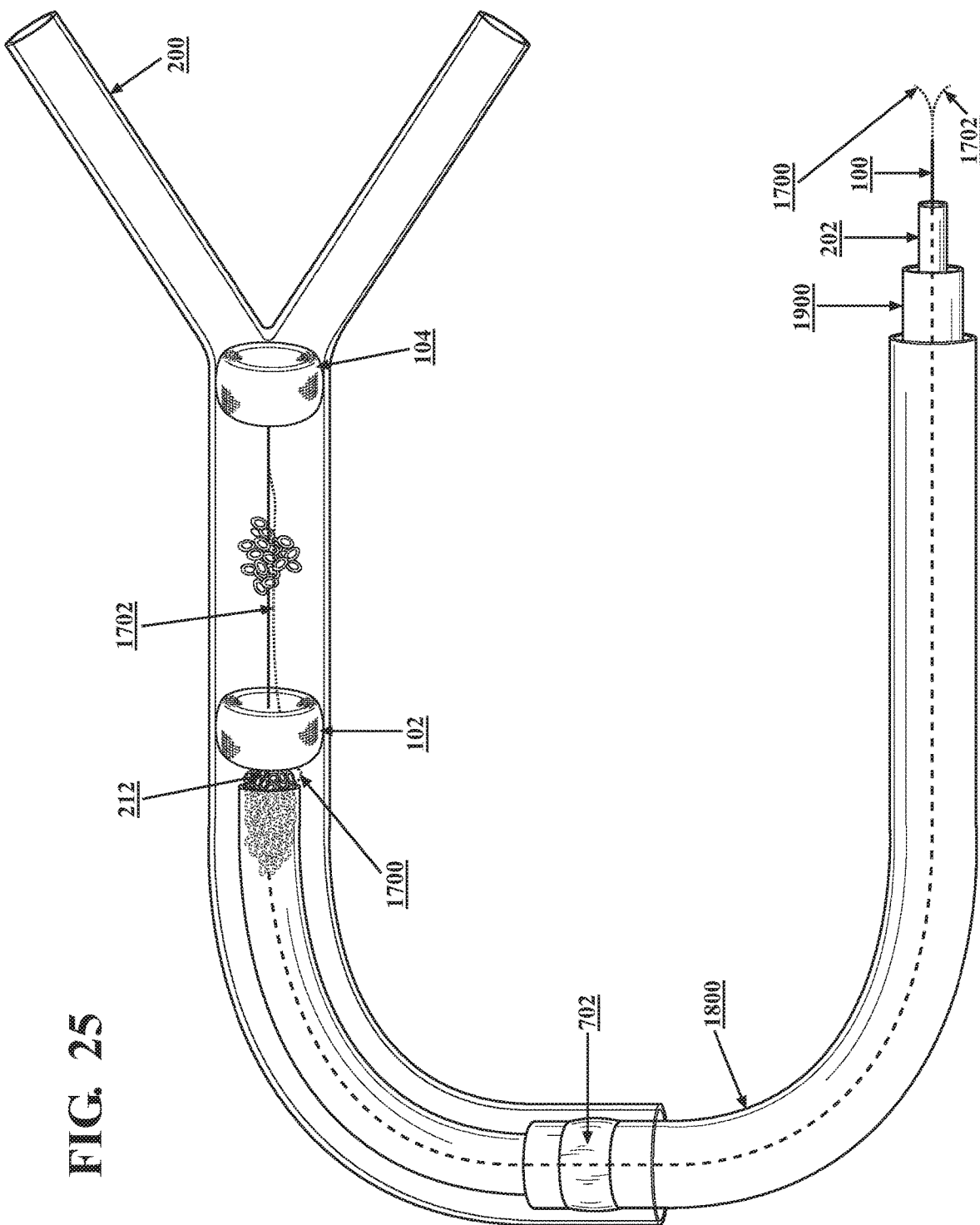

Once the distal body 104 opens at the M1 bifurcation, both superior and inferior M2 protection has been established (see FIGS. 24 and 25). Using a proximal tether 1700 and a distal tether 1702 that connect to the proximal body 102 and exit from the delivery wire 100 either via an opening in the outer surface or via the opening on the end of the delivery wire 100 (see FIGS. 17A and 17B), the proximal body 102 can be moved along the M1 and possibly ICA lumen back and forth (i.e., proximally and distally axially along the delivery wire) by pulling the ends of the tethers 1710, 1720 as described herein and as desired by the clinician to mobilize occlusion and loosen and draw it proximally towards the suction device. If the initial placement of the proximal body 102 is determined to be too far in the distal direction, the interventionist may use the proximal tether 1700 that is attached to the proximal body 102 to pull the proximal body 102 back in the proximal direction to place it farther from the distal end of the retrieval device. This allows the interventionist to adjust the proximal body's position along the wire 100 instead of only being able to advance the proximal body 102 in the distal direction. In an example, the proximal body 102 may have a Kevlar tether that exits the delivery wire (or hypo tube) 100 at an opening distance about 1-2 cm proximal to the proximal side of the proximal body 102 to which it is attached. Therefore, while the two bodies are initially adjacent to each other, the proximal body 102, once electrolytically detached, can be withdrawn a distance proximally along the delivery wire 100 axis 1-1.5 cm by pulling on the proximal tether 1700. (All distances herein may be adjusted according to the need). It may be advanced by pushing it forward with the delivery catheter 202 and/or a second, distal tether 1702 may exit the wire at opening 117B distally to the proximal body 102 which when pulled can pull the proximal body 102 distally back towards the distal body and adjacent to the opening 117B. Therefore, by pulling proximal tether 1700 and/or the distal tether 1702 the proximal body 102 may slide backwards and forwards along the delivery wire 100. In this example, this configuration provides the proximal body 102 with 1-1.5 cm of travel distance back and forth along the delivery wire 100. Despite anterograde flow, the distal body 104 may provide protection against distal embolization of loosened/floating occlusion thus eliminating/reducing the risk of distal embolization of this material (see FIG. 25).

Figure 26:
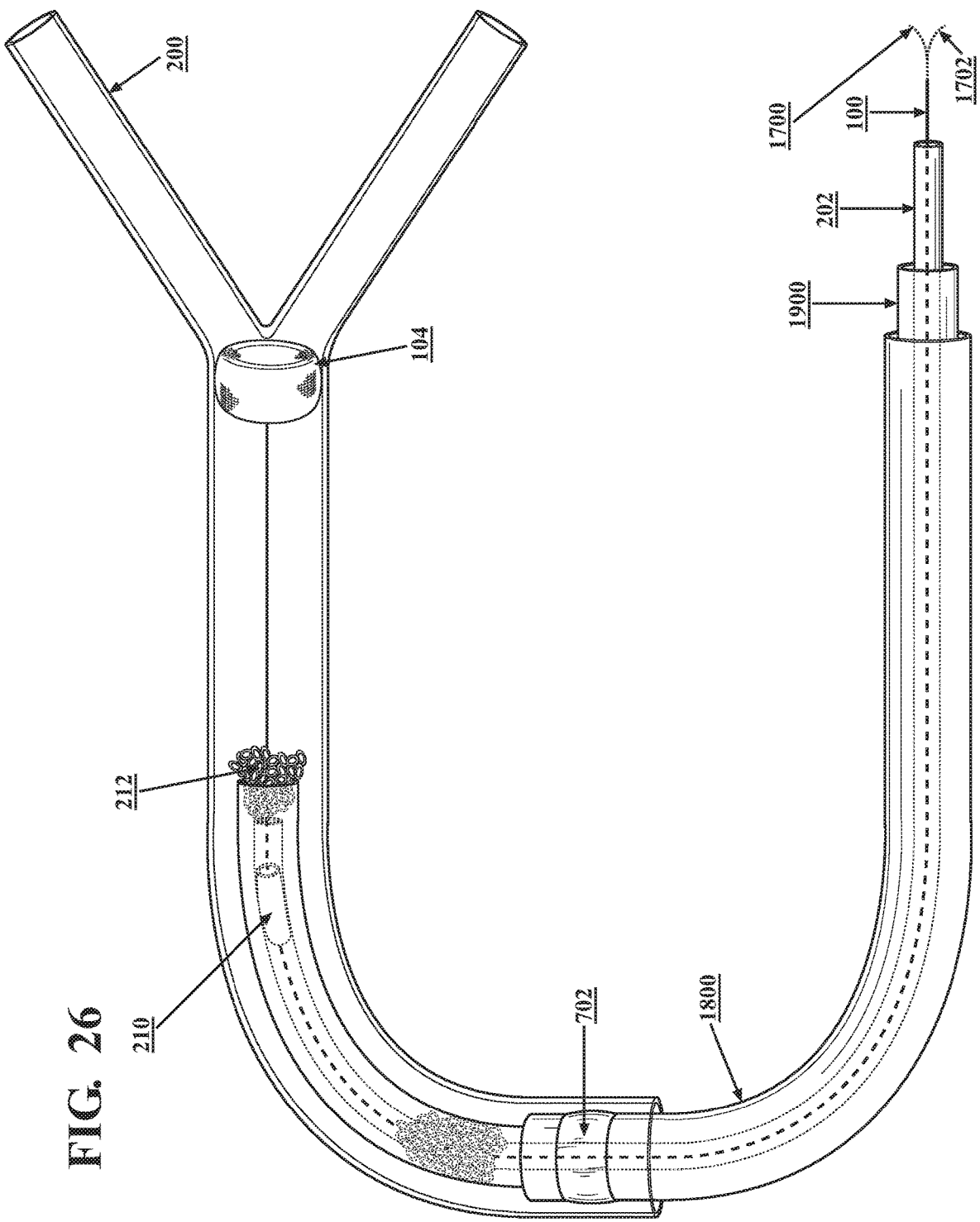
Figure 27:
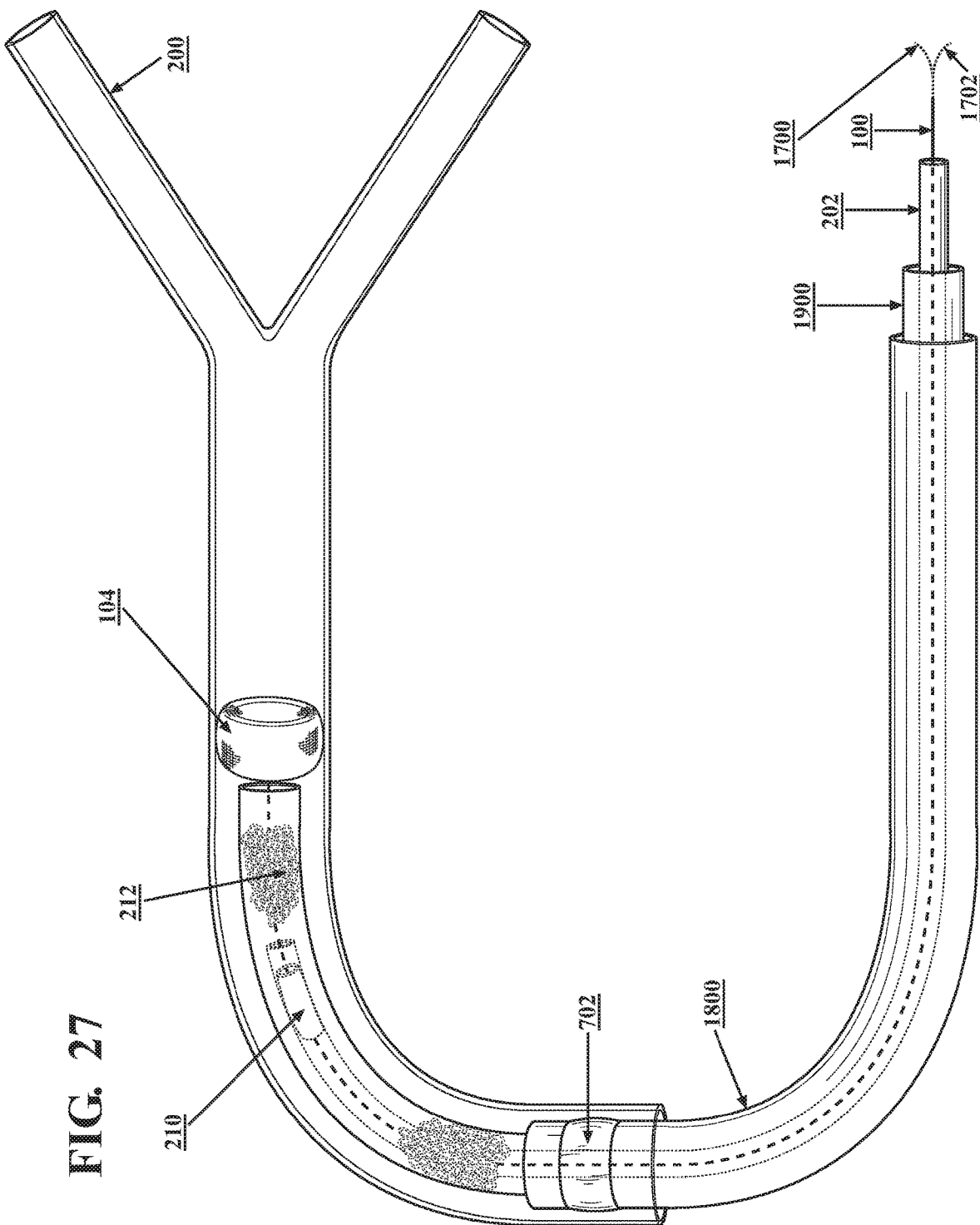

Once the thrombus 212 has been removed/evacuated through the access catheter 1900, the proximal and distal bodies can be removed by withdrawing them through the delivery catheter 202. This process will also mechanically draw any thrombus 212 that sits on the tip of the access catheter 1900 (cleans the catheter tip) into the catheter 1900 so that it does not embolize off the catheter tip and back into the intracranial circulation (see FIGS. 25-27).

In embodiments, the following steps may be followed for using the retrieval device, as described herein, for a foreign body (e.g., lost coil or fractured filter) capture and extraction intervention, such as an aneurysm coil lodged at an M1 bifurcation (proximal and distal bodies may be sized according to vessel size where the foreign body is located):

1. Guide catheter 1800 already in ICA from coiling procedure.
2. Advance a delivery catheter 202 distal to the foreign body.
3. Advance the retrieval device through the delivery catheter 202 (the "retrieval device", again is the delivery wire 100 with the proximal and distal bodies mounted thereon in a manner described in this disclosure).
4. When the distal body 104 reaches the end of the delivery catheter 202, the interventionist may optionally detach the releasable engagement of proximal body 102 so it is free to move axially along the delivery wire 100.
5. Pull the proximal tether 1700 and draw the proximal body 102 proximally in the delivery catheter 202 so that there is a space, in some embodiments a 1 cm space, between the two non-deployed bodies which are still constrained within the delivery catheter 202.
6. Slowly retract the delivery catheter 202 proximally. This will allow the distal body 104 to open in the vessel 200 distal to the foreign body.
7 Holding the wire in place, continue drawing the delivery catheter 202 proximally until the proximal body 102 is unsheathed. The proximal body 102 will now be opened proximal to the foreign body/coil.
8. The foreign body is now trapped/isolated between the distal and proximal bodies.
9. While holding the distal body 104 in place by holding the delivery wire 100, the proximal body 102 can now be approximated along the wire to the distal body 104 by either using the tethers as described herein or by simply pushing it forward with the delivery catheter 202 or drawing the distal body 104 proximally.
10. The foreign body/coil is now trapped between the two bodies and can be removed from the vessel 200. By pulling the entire system down to or into the guide catheter 1800.

What is claimed is:

1. A medical device for removing an occlusion from a vessel, comprising:
    a delivery catheter and a delivery wire,
    said delivery catheter comprising an internal lumen that extends through said delivery catheter, said internal lumen of said delivery catheter adapted to receive said delivery wire therein,
    said delivery wire comprising a distal end region, said delivery wire disposed in said internal lumen of said delivery catheter, said delivery wire further comprising a first body releasably engaged to said delivery wire at a first position on said delivery wire, said releasable engagement of said first body to said delivery wire comprising a breakable mechanical connection of said first body to said delivery wire, said breakable mechanical connection comprising a threshold holding force, said first body adapted to expand from a first compressed configuration to a first expanded configuration, said delivery wire further comprising a second body fixed to said delivery wire at a second position on said delivery wire, said second position comprising a position proximate said distal end region of said delivery wire and, thereby distal from said first position of said first body, said second body adapted to expand from a second compressed configuration to a second expanded configuration, said first body further adapted to disengage from said delivery wire and slidably translate along said delivery wire in a distal direction toward said second body when said delivery catheter is translated in a distal direction relative to said delivery wire, said delivery catheter contacts said first body and applies a force to said first body and, thereby, said breakable mechanical connection that is greater than said threshold holding force, whereby, when said first body is disposed on a proximal side of said occlusion and said second body is disposed on a distal side of said occlusion, said first body and said second body surround and contain said occlusion between said first and second bodies.

2. The medical device of claim 1, wherein said second body is adapted to be in said second compressed configuration when said second body is disposed in said internal lumen of said delivery catheter.

3. The medical device of claim 2, wherein said second body is adapted to be in said second expanded configuration when said second body is disposed outside said internal lumen of said delivery catheter.

4. The medical device of claim 1, wherein said first body is adapted to be in said first compressed configuration when said first body is disposed in said internal lumen of said delivery catheter.

5. The medical device of claim 4, wherein said first body is adapted to be in said first expanded configuration when said first body is disposed outside said internal lumen of said delivery catheter.

* * * * *